United States Patent [19]

Berger et al.

[11] 3,957,766
[45] May 18, 1976

[54] NOVEL NITROFURAN COMPOUNDS AND PHARMACEUTICAL COMPOSITIONS

[75] Inventors: Herbert Berger, Mannheim-Kafertal; Rudi Gall, Grobsachsen; Hartmut Merdes, Heidelberg; Kurt Stach, Mannheim-Waldhof; Winfriede Sauer, Mannheim-Wallstadt; Wolfgang Vomel, Mannheim, all of Germany

[73] Assignee: Boehringer Mannheim G.m.b.H., Mannheim, Germany

[22] Filed: Sept. 20, 1972

[21] Appl. No.: 290,682

Related U.S. Application Data

[63] Continuation-in-part of Ser. No. 151,944, June 10, 1971, abandoned.

[30] Foreign Application Priority Data

June 19, 1970   Germany............................ 2030218
Mar. 1, 1971    Germany............................ 2109577
Mar. 1, 1971    Germany............................ 2109570
Oct. 29, 1971   Germany............................ 2153902

[52] U.S. Cl................. 260/240.1; 260/247.1 L; 260/247.5 D; 260/250 A; 260/268 BC; 424/246; 424/250
[51] Int. Cl.²............. C07D 295/06; C07D 295/12; C07D 471/04
[58] Field of Search................ 260/250 A, 247.5 E, 260/247.1 L, 240.1, 268 BC, 247.5 D; 424/250, 246

[56] References Cited

UNITED STATES PATENTS

| | | | |
|---|---|---|---|
| 3,096,329 | 7/1963 | Steck | 260/250 A |
| 3,642,792 | 2/1972 | Bellasio et al. | 260/247.5 R |
| 3,644,335 | 2/1972 | Earley et al. | 260/239 BD |

FOREIGN PATENTS OR APPLICATIONS

1,123,247   8/1968   United Kingdom

OTHER PUBLICATIONS

C. F. Boehringer & Soehne, Chemical Abstracts, Vol. 67, 54151B, (1967).
Berger et al., Chemical Abstracts, Vol. 70, 57869q, (1969).
Burger, Medicinal Chemistry 3rd Ed., Pts. I & II.
Pollak et al., Chemical Abstracts, Vol. 70, 68290v, (1969).

*Primary Examiner*—Alton D. Rollins
*Assistant Examiner*—Jose Tovar
*Attorney, Agent, or Firm*—Burgess, Dinklage & Sprung

[57] ABSTRACT

Certain novel nitrofuran compounds of the formula:

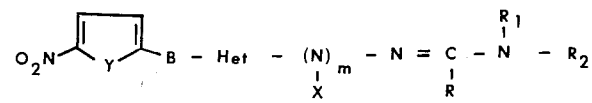

wherein
  Het is an aromatic heterocylic linkage;
  B is a bond or vinylene;
  Y is O or S;
  $m$ is 0 or 1;
  X is hydrogen, lower alkyl or alkanoyl; and
  the R's are variously defined;
are outstandingly effective bacteriostats and bactericides.

15 Claims, No Drawings

NOVEL NITROFURAN COMPOUNDS AND PHARMACEUTICAL COMPOSITIONS

This application is a continuation-in-part of Serial No. 151,944 filed June 10, 1971, now abandoned.

The present invention is concerned with new nitrofuran and nitrothienyl compounds and is also directed to pharmaceutical compositions containing the new nitrofuran (and nitrothienyl) compounds.

The new compounds according to the present invention are compounds of the general formula:

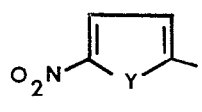 B — Het — (N)$_m$ — N=C — N — R$_2$   (I),
                                    |        |   |
                                    X        R   R$_1$ wherein Het signifies a diavalent heterocycle of aromatic character, optionally substituted by halogen, hydroxyl, azido, cyano, alkyl, alkoxy, alkylmercapto, or alkylamino, and is either (i) a five-membered ring containing two or three heteroatoms, at least one of which is a nitrogen atom, or (ii) a six-membered ring containing 1 – 3 nitrogen atoms, or (iii) a bicyclic system in which two of the rings according to (i) and/or (ii) are fused together in such a manner that a nitrogen atom is common to both rings, B being attached to a carbon atom being in the α-position in respect to a nitrogen in the Het ring system and the righthand side of the molecule being attached to another carbon atom in the Het ring system; Y is oxygen or sulfur; $m$ is 0 or 1, X is hydrogen, lower alkyl, or lower acyl, e.g., alkanoyl, B is a valency bond or, when $m$ is 1, can also be a vinylene linkage; R is hydrogen, lower alkyl, alkoxyalkyl, or alkylmercaptoalkyl and R$_1$ and R$_2$, which can be the same or different, are hydrogen, hydroxyl, lower alkyl, alkoxyalkyl, alkylmercaptoalkyl, lower hydroxyalkyl, mono(lower alkyl)-amino, or di-(lower alkyl)-amino, and an aryl- or aralkyl group optionally being substituted; or wherein R$_1$ or R$_2$, preferably only one of R$_1$ and R$_2$, is acyl (e.g., lower alkanoyl and carbamoyl), acylaminoalkyl, or carbalkoxyalkyl, or wherein two of the symbols R, R$_1$ and R$_2$ together with the nitrogen atom to which R$_1$ and R$_2$ are attached, form an aliphatic 5- or 6-membered ring, which can optionally contain one or two additional heteroatoms, such as oxygen, sulfur or nitrogen, in the ring, and which can optionally be substituted, preferably in the 4-position of the ring, with hydroxy, lower alkyl, or lower hydroxy alkyl; and the physiologically compatible salts thereof.

Thus, there are contemplated mono- or bicyclic heterocyclic ring systems containing from 1 to 3 nitrogen atoms per ring wherein, in the bicyclic structures, at least one of said nitrogens is common to both rings and wherein, in the bicyclic case, at least one ring preferably contains two or three nitrogen atoms. Further contemplated are such ring systems containing one or more, preferably one, hetero atom other than nitrogen, preferably oxygen or sulfur, as part of the ring system.

A group of compounds within the genus presented above, which is particularly preferred because of the exceptional and surprising degree of bacteriostatic activity they exhibit in urine are compounds wherein, in formula I, above, B is a valence bond, "Het" is a triazolopyridazine or thiadiazole system, $m$ is 0, R is hydrogen; and R$_1$ and R$_2$ are, individually, alkyl, acyl, acylaminoalkyl, cycloalkyl, carbalkoxyalkyl, or R$_1$ and R$_2$ together with the nitrogen atom to which they are attached, are morpholino, piperidino, 4-hydroxypiperidino, 4-alkylpiperidino, 4-hydroxyalkylpiperidino, piperazinyl, 4-alkylpiperazinyl, and 4-hydroxyalkylpiperazinyl.

This preferred group of compounds can thus be represented by the formula:

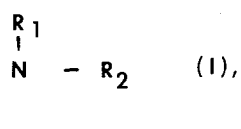 Het—N=CH—R'   (I')

wherein
Y is sulfur or oxygen,
Het is a triazolopyridazine or thiadiazole system, and
R' is di (lower) alkylamino, acylated amino (e.g., lower alkanoylamino or carbamoylamino), acylated amino (lower) alkylamino, carbalkoxyalkylamino, morpholino; or cycloalkylamino (of, e.g., 5 to 6 ring carbons), piperidino or piperazinyl optionally substituted in the 4-position by a hydroxyl groupo or by an alkyl or hydroxyalkyl radical;

as well as the pharmacologically compatible salts thereof.

Vinylene group-containing nitrofuran compounds substituted with amidine radicals are already known from German Pat. No. 1,545,708. However, in contradistinction thereto, the new compounds (I) according to the present invention are characterized by a surprising antimicrobial activity in urine and are, therefore, particularly suitable for the treatment of infections of the urinary tract.

The compounds (I) according to the present invention can be prepared, for example, by one of the following methods:

a. condensation of a compound of the general formula:

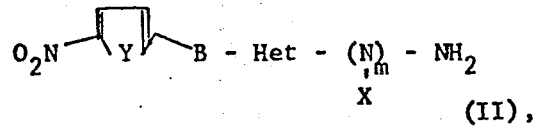

wherein Y, B, Het, X and $m$ have the same meanings as above, with a compound of the general formula:

in which R, R$_1$ and R$_2$ have the same meanings as above and Z is an oxygen or sulphur atom, or with a reactive derivative thereof; or b. reaction of a compound of the general formula

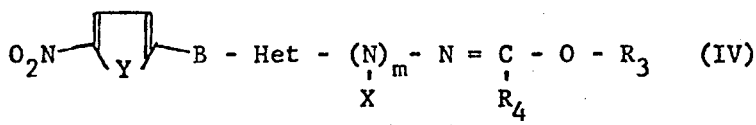

wherein Y, B, Het, X and *m* have the same meanings as above, $R_3$ is a lower alkyl radical and $R_4$ is a hydrogen atom or a lower alkyl radical, or of a salt thereof, with a compound of the general formula

wherein $R_1$ and $R_2$ have the same meanings as above; or c. nitration of a compound of the general formula:

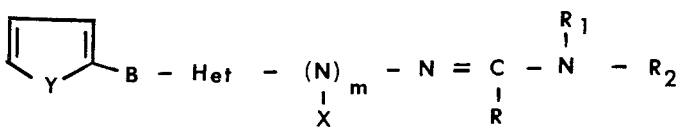

wherein Y, B, Het, X, *m*, R, $R_1$ and $R_2$ have the same meanings as above; or d. for the case in which B represents a vinylene linkage condensation of 5-nitrofuran-2-aldehyde or of 5-nitrothiophene-2-aldehyde or of a reactive derivative thereof with a compound of the general formula:

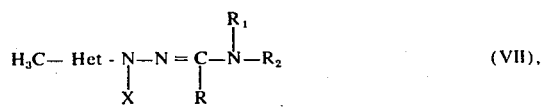

wherein Het, X, R, $R_1$ and $R_2$ have the same meanings as above.

When Z is an oxygen atom, the condensation of compounds of general formula (II) with compounds of general formula (III) expediently takes place in the presence of an agent splitting off water, preferably phosphorus oxychloride or thionyl chloride. When Z is a sulfur atom, the condensation can be carried out by warming in alcoholic solution.

As reactive derivatives of the compounds of general formula (III), there are especially suitable those compounds in which the carbonyl group is present in ketalized or acetalized form. In this case, the condensation usually takes place merely by warming the reaction components in an inert solvent, for example, dimethyl formamide.

When $R_1$ and/or $R_2$ in compounds of general formula (I) is to be a hydrogen atom, then as reactive derivatives of compounds of general formula (III) there can also be used imido ethers or imido thioethers either in the melt or in solution. The amine components is advantageously employed in the form of a salt, for example a hydrochloride.

When $R_1$ and $R_2$ in compounds of general formula (I) are to be hydrogen atoms, then there can be used the nitriles derived from compounds of general formula (III) in an inert solvent; the reaction of the nitriles in the melt with the p-toluene-sulphonates of the amines used is especially advantageous.

When one of the symbols $R_1$ and $R_2$ is to be hydrogen atom and Z is an oxygen atom, then the use of phosphorus pentachloride as condensation agent has been found to be particularly useful. In this case, the reaction of the compounds of general formula (III) takes place via the corresponding imide chlorides.

The compounds of general formula (IV) can be advantageously reacted with the amines of general formula (V) by warming in alcoholic solution. In some cases, the reactivity of the compounds of general formula (IV) can be increased by converting them, before the reaction, into the corresponding addition salts of mineral acids, for example, into the hydrochlorides.

The compounds of general formula (IV) used as starting materials can be obtained by the reaction of compounds of general formula (II) with appropriate ortho esters or by reaction of appropriate lower carbonyl derivatives, for example, of N-acetyl derivatives, with trialkoxonium fluoroborates.

The nitration of compounds of general formula (VI) takes place in the usual manner with the use of nitric acid in sulfuric acid and/or acetic anhydride at low temperatures.

As reactive derivatives of the aldehydes used in reaction (d), there can be used, for example, the diacyl derivatives, preferably the diacetates, which can be reacted with the compounds of general formula (VII) in, for example, acetic anhydride.

The pharmacologically compatible salts of the new compounds according to the present invention can be prepared by neutralization of the free amino group of the compounds (I) with non-toxic inorganic or organic acids. For this purpose, there can be used, for example, hydrochloric acid, sulphuric acid, phosphoric acid, hydrobromic acid, acetic acid, lactic acid, citric acid, oxalic acid, malic acid, salicylic acid, malonic acid, maleic acid, succinic acid or an alkyl-sulfonic acid.

The preferred new compounds according to the present invention defined by formula (I') above can be prepared, for example, by one of the following methods:

a. reaction of a compound of the general formula:

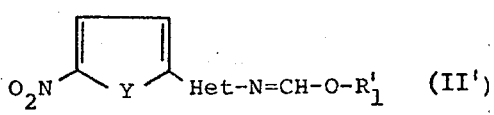

wherein Y and Het have the same meanings as above and $R_1'$ is a lower alkyl radical, or a salt thereof, with a compound of the general formula H.R'., wherein R' has the same meaning as above or b. condensation of a compound of the general formula:

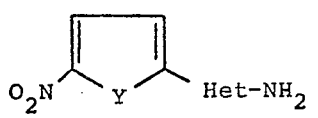

(III')

wherein Y and Het have the above-given meanings with a compound Z=CH—R', in which R' has the above given meanings and Z is an oxygen or sulphur atom, or with a reactive derivative thereof; or c. nitration of a compound of the general formula:

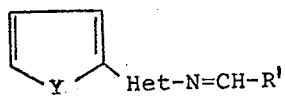

(IV')

wherein Y, Het and R' have the same meanings as above and, if desired, the compounds (I') obtained are converted into their pharmacologically compatible salts or the substituent R' is changed in known manner.

The compounds of (II') can be increased by converting them into corresponding addition salts of mineral acids, for example into hydrochlorides, prior to the reaction.

The compounds (II') used as starting materials can be prepared, for example, by the reaction of compounds of the general formula:

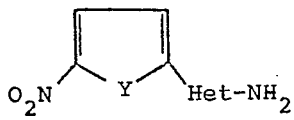

(III'')

wherein Y and Het have the above-given meanings, with appropriate ortho esters or by the reaction of corresponding lower carbonyl derivatives, for example, N-acetyl derivatives, with trialkoxonium fluoroborates.

When Z is an oxygen atom, the condensation of compounds of general formula (III') with compounds Z=CH—R' expediently takes place in the presence of an agent splitting off water, preferably phosphorus oxychloride or thionyl chloride. When Z is a sulfur atom, the condensation can be carried out by warming in alcoholic solution.

As reactive derivatives of the compounds Z=CH—R', there are especially suitable those compounds in which the carbonyl group is present in ketalized or actalized form. In this case, the condensation usually takes place merely by warming the reaction components in an inert solvent, for example, dimethyl formamide.

The nitration of compounds of general formula (IV) takes place in the usual manner with the use of nitric acid in sulphuric acid and/or acetic anhydride at low temperatures.

When the symbol R' is to represent an acylamino or cycloalkylamino radical in the end product, then these products can be prepared, after the production of the fundamental structure, by reaction of the amino group with conventional acylation agents, for example, with acid anhydrides or isocyanates, or with alkylation agents, for example, with alkyl halides.

The pharmacologically compatible salts can be prepared, for example, by neutralization of the basic compounds of general formula (I) with non-toxic inorganic or organic acids. For this purpose, there can be used, for example, hydrochlorid acid, sulfuric acid, phosphoric acid, hydrobromic acid, acetic acid, lactic acid, citric acid, oxalic cid, malic acid, salicyclic acid, malonic acid, maleic acid, succinic acid or alkyl-sulphonic acids.

The following Examples are given for the purpose of illustrating the present invention:

EXAMPLE 1

Preparation of 3-(5-nitro-2-furyl)-6-(dimethylaminomethyleneamino)-s-triazolo[4,3-b]pyridazine 1.6 ml. phosphorus oxychloride were added dropwise, with stirring, at 25°–30°C to 1.33 ml. anhydrous N,N-dimethyl formamide in 7 ml. anhydrous dioxan, stirring was continued for one hour, whereafter 2 g. crude 3-(5-nitro-2-furyl)-6-amino-s-triazolo[4,3]-b-pyridazine were added thereto, together with a further 5 ml. anhydrous dioxan. Stirring was continued for 1.5 hours at 30° to 35°C, whereafter the reaction mixture was poured on to ice, the pH value adjusted to 7 with an aqueous solution of ammonia, the precipitated crystals were filtered off with suction, washed with water and dried in a vacuum at 70°C. to give 2.2 g. of crude product. After recrystallization from 21 ml. dimethyl-formamide, there was obtained 1.65 g. yellow 3-(5-nitro-2-furyl)-6-(dimethylaminomethyleneamino)-s-triazolo[4,3-b]pyridazine, which had a melting point of 290° – 292°C.

The 3-(5-nitro-2-furyl)-6-amino-s-triazolo[4,3-b]-pyridazine used as starting material was prepared as follows:

6 g. of 3-hydrazino-6-chloropyridazine were dissolved in 20 ml. ethanol and 20 ml. water, 3 ml. glacial acetic acid were added thereto, the mixture was heated on a steambath until complete solution was obtained and then 4 g. furan-2-aldehyde were added, whereafter the reaction mixture was further heated for 10 minutes on a steambath, cooled and the precipitated crystals filtered off with suction. These crystals were washed with a mixture of equal volumes of water and ethanol and finally with ether. There were thus obtained 8.8 g. crude 3-furfurylidene-hydrazino-6-chloropyridazine, which had a melting point of 222° – 225°C. Subsequently, 4 g. 3-furfurylidene-hydrazino-6-chloropyridazine were introduced, with stirring, at 70°C. into a solution of 25 g. ferric chloride hexahydrate in 80 ml. dioxan. Stirring was continued for 3 hours at 75° – 80°C., whereafter the dioxan was evaporated off in a vacuum, the evaporation residue was triturated with 70 ml. water and, after standing in the cold, the solid product was filtered off with suction and dried in a vacuum at 80°C. There were obtained 3 g. crude 3-(2-furyl)-6-chloro-s-triazolo-[4,3-b]pyridazine, which had a melting point of 174° – 178° C.

29.9 g. 3-(2-furyl)-6-chloro-s-triazolo[4,3-b]pyridazine were stirred for 5 hours at 125° – 130°C. in an autoclave with 300 ml. aqueous ammonia solution saturated at 0° to −5°C. After cooling, the precipitated product was filtered off with suction, washed with water to give, after drying, 23.9 g. of a solid substance which was dissolved, with heating, in 300 ml. methanol. The methanolic solution was treated with activated charcoal and then hot filtered. After evaporation of the filtrate in a vacuum, there were obtained 22.3 g. crude 3-(2-furyl)-6-amino-s-triazolo[4,3-b]pyridazine (m.p. 214° – 216°C.) which was heated under reflux for 30 minutes in 223 ml. acetic anhydride. After cooling to 0° to –5°C., there was added dropwise into the suspension obtained, in the course of about 30 minutes, a mixture, prepared at –10°C., of 50 ml. concentrated sulfuric acid and 3.15 g. 100% nitric acid. The reaction mixture was further stirred for 1 hour at 0° to –5°C., subsequently poured on to ice, the precipitated yellow, crude 3-(5-nitro-2-furyl)-6-acetamido-s-triazolo[4,3-b]pyridazine filtered off with suction, washed with water and dried. The yield was 22.17 g. and the compound melted, with decomposition, at 296° – 298°C.

10 g. of the compound thus obtained were boiled under reflux for one hour with 50 ml. glacial acetic acid and 50 ml. 5N hydrochloric acid, the reaction mixture then evaporated in a vacuum, the evaporation residue triturated with 50 ml. of water, mixed with a concentrated aqueous solution of ammonia until a clearly basic reaction was obtained, thoroughly stirred, undissolved material filtered off with suction, thereafter washed with water and dried in a vacuum at 80°C. There were obtained 8 g. crude 3-(5-nitro-2-furyl)-6-amino-s-triazolo-[4,3-b]pyridazine, which melted with decomposition at 310° – 315°C.

EXAMPLE 2

Preparation of N[3-(5-Nitro-2-furyl)-6-(s-triazolo[4,3-b]pyridazinyl)]-N',N'-dimethyl-acetamidine 0.8 ml. phosphorus oxychloride were added dropwise, with stirring, at 25° – 30°C. to 0.8 ml. N,N-dimethyl-acetamide in 3.5 ml. anhydrous dioxan. The reaction mixture was stirred for 1 hour and then 1 g. crude 3-(5-nitro-2-furyl)-6-amino-s-triazolo[4,3-b]pyridazine added thereto, whereafter the reaction mixture was further stirred for 1.5 hours at 30° – 35°C. and then worked up in the manner described in Example 1. In this way, there were obtained 0.6 g. N-[3-(5-nitro-2-furyl)-6-(s-triazolo[4,3-b]pyridazinyl)]N',N'-dimethyl-acetamidine, which had a melting point of 278° – 280°C.

EXAMPLE 3

Preparation of 3-(5-Nitro-2-furyl)-6-[(-piperidinylmethyl)-methyleneamino]-s-triazolo[4,3-b]pyridazine.

1.6 ml. phosphorus oxychloride were added at 30° – 35°C. to 2.2 ml. N-acetyl-piperidine in 7 ml. anhydrous dioxan, the reaction mixture stirred for 1 hour at this temperature and then 2 g. 3-(5-nitro-2-furyl)-6-amino-s-triazolo[4,3-b]pyridazine added thereto, whereafter the reaction mixture was further stirred for 1.5 hours at 35° – 40°C., poured on to ice, insoluble material filtered off with suction, the filtrate rendered alkaline with a concentrated aqueous solution of ammonia, the precipitate product filtered off with suction, washed with water and dried in a desiccator. After recrystallization from 12 ml. 70% aqueous dimethyl formamide, with the use of activated charcoal and subsequent drying, in a vacuum at 120°C., there were obtained 0.63 g. 3-(5-nitro-furyl)-6-[(1-piperidinyl-methyl)methyleneamino]-s-triazolo[4,3-b]pyridazine, which had a melting point of 207° – 209°C.

EXAMPLE 4

Preparation of 3-(5-Nitro-2-furyl)-5-(dimethylaminomethyleneamino)-1,2,4-thiadiazole.

From 1.33 ml. anhydrous N,N-dimethyl formamide, 7 ml. anhydrous dioxan, 1.6 ml. phosphorus oxychloride and 2 g. 3-(5-nitro-2-furyl)-5-amino-1,2,4-thiadiazole, there were obtained, in the manner described in Example 1, 2,24 g. of crude product which, after recrystallization from 30 ml. dioxane with the use of activated charcoal, gave 1.35 g. 3-(5-nitro-2-furyl)-5-(dimethylaminomethyleneamino)-1,2,4-thiadiazole, which had a melting point of 211° – 213°C.

The 3-(5-nitro-2-furyl)-5-amino-1,2,4-thiadiazole used as starting material was prepared in the following manner:

32.7 g. crude 5-nitro-2-furamidine hydrochloride (m.p. 232° – 234°C.) were suspended in 910 ml. anhydrous acetone, 32 g. trichloromethyl-sulfenyl chloride were added thereto while stirring, whereafter 91 ml. triethylamine were added dropwise at 0° – 5°C. within the course of 20 minutes, the reaction mixture stirred for 40 minutes and thereafter for 2 hours at 50° – 55°C. After cooling, the precipitated triethylamine hydrochloride was filtered off with suction, the filtrate evaporated in a vacuum, the evaporation residue triturated with water, adjusted to a pH of about 5 with sodium acetate, undissolved material filtered off with suction, the still moist material triturated with methanol, filtered with suction, washed with methanol and then dried in a vacuum at 80°C. to give 17.5 g. crude 3-(5-nitro-2-furyl)-5-chloro-1,2,4-thiadiazole (m.p. 160° – 162°C.) which can be recrystallized from methanol-dioxan (1:1), with the use of activated charcoal, whereafter it melts at 167° – 168°C.

13.8 g. of the crude product thus obtained were dissolved in a mixture of 500 ml. ethanol and 150 ml. dioxan and ammonia gas passed in, while stirring, for 4 hours at 70°C., whereafter the solution was mixed with activated charcoal, suction filtered while still hot, the clear filtrate concentrated in a vacuum to about 70 ml., the precipitated crystals filtered off with suction, washed with ethanol, water and, finally, with ether to give 7.5 g. crude 3-(5-nitro-2furyl)-5-amino-1,2,4-thiadiazole, which melted, with decomposition, at 277° – 278°C.

EXAMPLE 5

Preparation of 1-Methyl-2-[3-(5-nitro-2-furyl)-6-(s-triazolo[4,3-b]pyridazinyl)]-imino-pyrrolidine.

0.8 ml. phosphorus oxychloride were added at 25° – 30°C. to 0.85 ml. N-methyl-pyrrolidone in 3.5 ml. anhydrous dioxan the mixture stirred for 1 hour and then 1 g. 3-(5-nitro-2-furyl)-6-amino-s-triazolo[4,3-b]pyridazine added, the preparation of which is described in Example 1. After stirring the reaction mixture for a further 1.5 hours at 35° – 40°C., it was poured on to ice, undissolved material was filtered off with suction, the filtrate was rendered alkaline with a concentrated aqueous solution of ammonia, the precipitated product was filtered off with suction, washed with water, dried and crystallized from 13 ml. dimethyl formamide, with the use of activated charcoal. There was obtained 0.42 g. 1-methyl-2-[3-(5-nitro-2-furyl)-6-

(s-triazolo-[4,3-b]pyridazinyl)]-imino-pyrrolidine, which had a melting point of 269° – 270°C.

EXAMPLE 6

Preparation of N-[3-(5-nitro-2-furyl)-7-methyl-5-(s-triazolo[4,3-c]pyrimidinyl)]-N',N'-dimethyl-formamidine.

0.8 ml. phosphorus oxychloride were added to 0.67 ml. anhydrous N,N-dimethyl formamide in 3.5 ml. anhydrous dioxan, the mixture then mixed for 1 hour at 25° – 30°C., whereafter 1 g. 3-(5-nitro-2-furyl)-7-methyl-5-amino-s-triazolo[4,3-c]-pyrimidine were added thereto. The reaction mixture was stirred for 1.5 hours at 40° – 45°C., poured on to ice, the pH adjusted to 8 – 9 with a concentrated aqueous solution of ammonia, undissolved material was filtered off with suction, washed with water, dried in a vacuum and recrystallized from 12 ml. dimethyl formamide/water (1:1), with the use of activated charcoal. There were obtained 0.54 g. N-[3-(5-nitro-2-furyl)-7-methyl-5-(s-triazolo[4,3-c]pyrimidinyl)]-N',N'-dimethyl-formamidine, which had a melting point of 205° – 207°C.

The 3-(5-nitro-2-furyl)-7-methyl-5-amino-s-triazolo[4,3-c]pyrimidine used as starting material was prepared in the following manner:

13.9 g. crude 2-amino-4-hydrazino-6-methyl-pyrimidine (m.p. 221°C.) were dissolved in a mixture of 50 ml. water and 7 ml. glacial acetic acid and briefly heated with a solution of 15.5 g. 5-nitro-furan-2-aldehyde in 50 ml. methanol on a streambath. After cooling, the precipitated crystals were filtered off with suction, washed with 50% aqueous methanol and then with ether. There were thus obtained 19.85 g. of crude hydrazone.

This hydrazone was introduced portionwise, with stirring at 50°C., into a solution of 40 g. lead tetraacetate in 500 ml. glacial acetic acid, stirring was continued at this temperature for 15 minutes and then the solution was almost completely evaporated in a vacuum, the evaporaton residue was triturated with about 250 ml. water, undissolved material was filtered off with suction, washed with water and dried to give 9.2 g. crude 3-(5-nitro-2-furyl)-5-amino-7-methyl-s-triazolo[4,3-c]-pyrimidine. A sample of this orange-yellow material was recrystallized from 70% aqueous dimethyl formamide, whereafter it melted at 325°C., with foaming, a colour change occured at about 210°C.

EXAMPLE 7

Preparation of N'-[2-(5-Nitro-2-furyl)-4-methyl-6-pyrimidinyl]-N,N-dimethyl-formamidine.

2-(5-Nitro-2-furyl)-4-methyl-6-aminopyrimidine was reacted, in the manner described in Example 1, with an adduct of dimethyl formamide and phosphorus oxychloride. There was obtained a paper chromatographically homogeneous, yellow crystalline substance which, after crystallization from methanol, melted at 165° – 168°C. Elementary analysis and spectral analysis confirmed the structure, i.e. that it was N'-[2-(5-nitro-2-furyl)-4-methyl-6-pyrimidinyl]-N,N-dimethyl-formamidine.

The 2-(5-nitro-2-furyl)-4-methyl-6-aminopyrimidine used as starting material was prepared in the following manner:

2-(2-Furyl)-4-methyl-6-chloropyrimidine was reacted in an autoclave at 150°C. with aqueous ammonia. The 2-(2-furyl)-4-methyl-6-amino-pyrimidine (m.p. 176° – 178°C.) so obtained was nitrated in acetic anhydride in the usual manner with a mixture of nitric acid, acetic anhydride and concentrated sulfuric acid. After hydrolysis of the product so obtained (m.p. 199° – 204°C.) with alcoholic hydrochloric acid and subsequent neutralization, there was obtained 2-(5-nitro-2-furyl)-4-methyl-6-amino-pyrimidine which melted, with decomposition, at 251° – 255°C.

EXAMPLE 8

Preparation of 2-(5-Nitro-2-furyl)-4-(2-dimethylaminomethylene-1-methyl)-hydrazino-pyrimidine.

In a manner analogous to that described in Example 1, by the reaction of 2-(5-nitro-2-furyl)-4-(1-methylhydrazino)-pyrimidine (m.p. 189° – 191°C.) (prepared from 2-(5-nitro-2-furyl)-4-chloropyrimidine (m.p. 211° – 215°C.) with methylhydrazine) with a dimethyl formamide-phosphorus oxychloride adduct, there were obtained red-violet crystals of 2-(5-nitro-2-furyl)-4-(2-dimethylaminomethylene-1-methyl)-hydrazino-pyrimidine, which melted, with decomposition, at 218°C. The elementary and spectral analysis confirmed the structure.

EXAMPLE 9

Preparation of 5-Cyano-6-dimethylaminomethyleneamino-2-methyl-4-(5-nitro-2-furyl)-pyrimidine.

In a manner analogous to that described in Example 1, by the reaction of 5-amino-5-cyano-2-methyl-4-(5-nitro-2-furyl)-pyrimidine with a dimethyl formamide-phosphorus oxychloride adduct, there was obtained 5-cyano-6-dimethylaminomethyleneamino-2-methyl-4-(5-nitro-2-furyl)-pyrimidine, which had a melting point of 202° – 204°C. The pale yellow crystals darkened when exposed to light.

The 6-amino-5-cyano-2-methyl-4-(5-nitro-2-furyl)-pyrimidine (m.p. 292° – 294°C.) used as starting material was obtained by the nitration of 6-amino-5-cyano-4-(2-furyl)-2-methyl-pyrimidine (m.p. 317° – 320°C.), which was obtained by the condensation of acetamidine with 1,1-dicyano-2-amino-2-(2-furyl)-ethylene.

EXAMPLE 10

Preparation of 3-(5-Nitro-2-furyl)-6-(dimethylaminomethylene-hydrazino)-s-triazolo[4,3-b]pyridazine.

0.96 ml. of phosphorus oxychloride was added dropwise, with stirring, at 25° – 30°C. to 0.84 ml. anhydrous N,N-dimethyl formamide in 4.2 ml. anhydrous dioxan, whereafter the reaction mixture was stirred for 1 hour at this temperature and then 1.56 g. crude 3-(5-nitro-2-furyl)-6-hydrazino-s-triazolo[4,3-b]-pyridazine were added thereto. The reaction mixture was stirred for 2.5 hours and then mixed with 60 ml. of a mixture of water and ice. The pH of the solution obtained was adjusted to about 8 with a concentrated aqueous solution of ammonia. There was obtained 1.35 g. of a precipitate which was recrystallized from about 70 ml. of a mixture of 50% dioxane, 45% dimethyl formamide and 5% water, with the use of activated charcoal. The yield of 3-(5-nitro-2-furyl)-6-(dimethylaminomethylenehydrazino)-s-triazolo[4,3-b]pyridazine amounted to 0.4 g. This compound melted, with foaming, at 278° – 279°C.

The 3-(5-nitro-2-furyl)-6-hydrazino-s-triazolo[4,3-b]-pyridazine used as starting material was prepared in the following manner:

35.5 g. 3-(5-nitro-2-furyl)-6-chloro-s-triazolo[4,3-b]-pyridazine were dissolved in 535 ml. hot 80% aqueous dioxan, 20 ml. hydrazine hydrate were added portionwise with stirring at 70°C., stirring continued for 10 minutes at 70°C. and the reaction mixture cooled. The material which precipitated was filtered off with suction, washed with water and dried to give 24 g. crude 3-(5-nitro-2-furyl)-6-hydrazino-s-triazolo[4,3-b]-pyridazine which, after recrystallization from 80% dimethyl formamide and 20% dioxan, melted, with foaming, at 261° –262°C.

The preparation of 3-(5-nitro-2-furyl)-6-chloro-s-triazolo[4,3-b]pyridazine was carried out by the oxidative cyclization of 1-(5-nitro-furfurylidene)-2-(3-chloro-6-pyridazinyl) hydrazine (m.p. 250° – 254°C.) with lead tetraacetate. The yield was 79% and the product, after recrystallization from dimethyl formamide, melted at 222° – 226°C.

EXAMPLE 11

Preparation of
5-(5-Nitro-2-furyl)-3-(dimethylaminomethyleneamino)-1,2,3-triazole.

From 2 g. crude 5-(5-nitro-2-furyl)-3-amino-1,2,4-triazole, which melted, with foaming, at 260° – 263°C., there were obtained, in a manner analogous to that described in Example 1 but without the second addition of dioxan and with neutralization with sodium acetate to a pH of 4 – 5, 2.1 g. crude 5-(5-nitro-2-furyl)-3-(dimethylaminomethyleneamino)-1,2,4-triazole which, after recrystallization from 70% aqueous dimethyl formamide, melted at 239° – 241°C.

EXAMPLE 12

Preparation of
2-(5-Nitro-2-furyl)-4-(2-dimethylamino-methylene)-hydrazino-pyrimidine.

Variant A:

A mixture of 0.5 g. 2-(5-nitro-2-furyl)-4-hydrazinopyrimidine, 1.0 g. dimethyl formamide-diethyl acetal and 1 ml. dimethyl formamide was heated to 100°C. for 2 hours. Thereafter, the starting material can no longer be detected on a thin layer chromatogram. The reaction solution was cooled and diluted with water. The crystals which precipitate out were filtered off with suction and washed with water, methanol and, finally, with ether. There was thus obtained 0.15 g. of red-brown crystals of 2-(5-nitro-2-furyl)-4-(2-dimethylaminomethylene)-hydrazino-pyrimidine which, after recrystallization from dimethyl formamide and water, decomposed at 215°C.

The 2-(5-nitro-2-furyl)-4-hydrazino-pyridimine used as starting material was prepared in the following manner:

2-(2-Furyl)-4-chloropyrimidine was reacted with hydrazine hydrate and subsequently boiled with acetic anhydride and nitrated. The 2-(5-nitro-2-furyl)-4-triacetylhydrazino-pyridimine (m.p. 174° – 176°C) so obtained was suspended in 6N hydrochloric acid. The reaction mixture was subsequently stirred for 1 hour at 100°C., whereby solution was obtained. After the addition of activated charcoal, it was filtered and the cooled solution was neutralized. The crystals which were obtained were filtered off with suction, washed and dried. There was obtained a yield of 75% of theory of pure 2-(5-nitro-2-furyl)-4-hydrazino-pyrimidine which, after recrystallization from aqueous dimethyl formamide, melted at 220° – 222°C.

Variant B:

2-(5-Nitro-2-furyl)-4-hydrazino-pyrimidine was reacted with a dimethyl formamide-phosphorus oxychloride adduct in a manner analogous to that described in Example 1. There was again obtained 2-(5-nitro-2-furyl)-4-(2-dimethylaminomethylene)-hydrazino-pyrimidine in good yield.

EXAMPLE 13.

Preparation of
1-Methyl-2-[2-(5-nitro-2-furyl)-4-pyrimidinyl]-hydrazino-pyrrolidine 2.08 ml. 1-methyl-2-pyrrolidone were dissolved in 8.6 ml. anhydrous dioxan, 1.92 ml. phosphorus oxychloride were added dropwise and the mixture was stirred for 1 hour at 25° – 30°C. 2.2 g. 2-(5-nitro-2-furyl)-4-hydrazino-pyrimidine were then added, a further 6.2 ml. anhydrous dioxan were added and the reaction mixture stirred for 1.5 hours at 30° – 35°C. The reaction mixture was then poured on to ice, filtered with activated charcoal and neutralized with a dilute aqueous solution of ammonia. There were thus obtained 2.6 g. (87% of theory) of a red-brown product, which was recrystallized from dioxan. There was thus obtained 1-methyl-2-[2-(5-nitro-2-furyl)-4-pyrimidinyl]-hydrazino-pyrrolidine, which melted at 175° – 177°C. The spectral and elementary analysis confirmed the structure.

EXAMPLE 14.

Preparation of
2-(5-Nitro-2-furyl)-4-[2-(dimethylaminomethyl)-methylene]-hydrazino-pyrimidine.

2-(5-Nitro-2-furyl)-4-hydrazino-pyrimidine was reacted with the adduct obtained from N,N-dimethyl-acetamide and phosphorus oxychloride in the manner described in Example 1. There were obtained red-brown crystals of 2-(5-nitro-2-furyl)-4[2-(dimethylaminomethyl)-methylene]-hydrazino-pyrimidine which, after recrystallization from dioxan, melted at 214° – 217°C.

EXAMPLE 15

Preparation of
2-(5-Nitro-2-furyl)-4-[2-(dimethylamino-methoxymethyl)-methylene]-hydrazino-pyrimidine.

1.2 g. N,N-dimethyl-methoxy-acetamide were dissolved in 4.3 ml. dry dioxan and mixed at ambient temperature with 0.96 ml. phosphorus oxychloride. After stirring for 1 hour at 25° – 30°C., there was added 1.1 g. 2-(5-nitro-2-furyl)-4-hydrazino-pyrimidine and 3.1 ml. dry dioxan, whereafter the suspension was further stirred for 1.5 hours at 30° – 35°C. The reaction mixture was then poured on to ice, the solution obtained mixed with activated charcoal and filtered and neutralized. The precipitated red-brown crystals were thin layer chromatographically homogeneous and melted at 132° – 135°C. There were obtained 0.7 g.

(44% of theory) 2-(5-nitro-2-furyl)-4-[2-(dimethylaminomethoxymethyl)-methylene]-hydrazino-pyrimidine. The spectral and elementary analysis confirmed the structure.

EXAMPLE 16.

Preparation of 2-(5-Nitro-2-furyl)-4-chloro-5-methyl-6-(2-dimethylamino-methylene)-hydrazino-pyrimidine.

2-(5-Nitro-2-furyl)-4-chloro-5-methyl-6-hydrazino-pyrimidine was reacted with the adduct obtained from N,N-dimethyl-formamide and phosphorus oxychloride in the manner described in Example 1. There was thus obtained 2-(5-nitro-2-furyl)-4-chloro-5-methyl-6-(2-dimethylaminomethylene)-hydrazino-pyrimidine which melted, with decomposition, at 220°C.

The 2-(5-nitro-2-furyl)-4-chloro-5-methyl-6-hydrazino-pyrimidine used as starting material, which melted, with decomposition, at 228°C., was prepared in the following manner:

2-(2-Furyl)-4,6-dichloro-5-methyl-pyrimidine, obtained by the reaction of 2-(2-furyl)-4,6-dihydroxy-5-methyl-pyrimidine with phosphorus oxychloride, was nitrated with acetyl nitrate in sulfuric acid and the 2-(5-nitro-2-furyl)-4,6-dichloro-5-methyl-pyrimidine (m.p. 174° – 175°C.) thus obtained was subsequently reacted in isopropanol with hydrazine hydrate.

In an analogous manner, there was prepared 2-(5-nitro-2-furyl)-4-azido-6-(2-dimethylaminomethylene)-hydrazino-pyrimidine, which melted, with decomposition, at 196° – 198°C.

As starting material, there was used 2-(5-nitro-2-furyl)-4-azido-6-hydrazinopyrimidine, which melted, with decomposition, at 189° – 191°C. This compound was prepared in the following way:

2-(2-Furyl)-4,6-dichloropyrimidine (m.p. 68° – 70°C.) was reacted with sodium azide in aqueous acetone to give 2-(2-furyl)-4-azido-6-chloropyrimidine (m.p. 117° – 119°C.) and this was then nitrated to give 2-(5-nitro-2-furyl)-4-azido-6-chloropyrimidine (m.p. 114° – 116°C.) which was, in turn, reacted with hydrazine hydrate in isopropanol.

EXAMPLE 17.

Preparation of 2-[2-(5-Nitro-2-furyl)-vinyl]-5-(2-dimethylaminomethylene)-hydrazino-1,3,4-thiadiazole.

In a manner analogous to that described in Example 1, from 2.5 g. crude 2-[2-(5-nitro-2-furyl)-vinyl]-5-hydrazino-1,3,4-thiadiazole, there were obtained 2.1 g. 2-[2-(5-nitro-2-furyl)-vinyl]-5-(2-dimethylaminomethylene)-hydrazino-1,3,4-thiadiazole which was recrystallized from 95% aqueous dioxan, with the use of activated charcoal, whereafter it had a melting point of 205° – 206°C.

The 2-[2-(5-nitro-2-furyl)-vinyl]-5-hydrazino-1,3,4-thiadiazole used as starting material, was prepared in the following manner:

3.35 g. 2-[2-(5-nitro-2-furyl)-vinyl]-5-amino-1,3,4-thiadiazole were dissolved, with warming, in 500 ml. dioxan/concentrated hydrochloric acid (1:1). A solution of 2.5 g. sodium nitrite in 20 ml. water was added dropwise at 70°C. Within the course of 10 minutes, the reaction mixture was then stirred for 10 minutes, the dioxan subsequently distilled off in a vacuum and the residue left to stand for 30 minutes at ambient temperature. After suction filtration and washing out with water, the residue of about 3.9 g. was boiled up with 100 ml. dioxan and insoluble material filtered off. From the cooled filtrate, there was obtained 1.9 g. 2-[2-(5-nitro-2-furyl)-vinyl]-5-chloro-1,3,4-thiadiazole, which had a melting point of 215° – 216°C. 5 g. of this chloro compound in a hot mixture of 310 ml. dioxan and isopropanol (1:1) were mixed at 70°C. with a solution of 4 ml. hydrazine hydrate in dioxan/isopropanol (1:1). After 2 minutes, the reaction mixture was cooled to ambient temperature and then stirred for 2 hours, whereafter it was filtered with suction and the solid material washed with solvent and then successively purified with water and ether. There were thus obtained about 2.8 g. 2-[2-(5-nitro-2-furyl)-vinyl]-5-hydrazino-1,3,4-thiadiazole, which melted, with decomposition, at 234° – 235°C.

EXAMPLE 18.

Preparation of 2-(5-Nitro-2-furyl)-4-(2-dimethylaminomethylene)-hydrazino-pyrimidine.

0.1 g. 2-(5-nitro-2-furyl)-4-(2-ethoxy-methylene)-hydrazino-pyrimidine (m.p. 208° – 213°C.), prepared from 2-(5-nitro-2-furyl)-4-hydrazino-pyrimidine by warming with orthoformic acid ethyl ester and recrystallization of the crude product from dioxan, were suspended with 0.03 g. dimethyl ammonium chloride in 3 ml. alcohol and stirred under reflux. After passing in dry, gaseous dimethylamine, there was obtained a solution in which, after one hour, no more starting material can be detected chromatographically. The 2-(5-nitro-2-furyl)-4-(2-dimethylaminomethylene)-hydrazino-pyrimidine so obtained was the same as the product obtained in Example 12 and decomposed at 215°C.

EXAMPLE 19.

Preparation of 3-(5-Nitro-2-thienyl)-6-(2-dimethylaminomethylene)-hydrazino-s-triazolo[4,3-b]-pyridazine.

In a manner analogous to that described in Example 1, by the reaction of 3-(5-nitro-2-thienyl)-6-hydrazino-s-triazolo-[4,3-b]pyridazine (m.p. 257° – 259°C.; decomp.) with dimethyl formamide-phosphorus oxychloride adduct, there was obtained 3-(5-nitro-2-thienyl)-6-(2-dimethylaminomethylene)-hydrazino-s-triazolo[4,3-b]pyridazine which, when boiled out with dioxan and collected as insoluble residue, melted at 266° – 268°C.

The 3-(5-nitro-2-thienyl)-6-hydrazino-s-triazolo[4,3-b]-pyridazine used as starting material was prepared in the following manner:

3-Hydrazino-6-chloropyridazine was condensed with 5-nitro-2-thiophene-aldehyde in ethanol and the 3-(5-nitro-2-thienylidene-hydrazino)-6-chloropyridazine (m.p. 306° – 308°C. decomp.) thus obtained was cyclized in glacial acetic acid with lead tetraacetate to give 3-(5-nitro-2-thienyl)-6-chloro-s-triazolo[4,3-b]pyridazine (m.p. 215° – 217°C.) and this subsequently reacted with hydrazine hydrate in isopropanol.

EXAMPLE 20.

Preparation of 2-(5-Nitro-2-furyl)-4-[2-(diethylaminomethyl)-methylene]-hydrazino-pyrimidine.

2-(5-Nitro-2-furyl)-4-hydrazino-pyrimidine was reacted with the adduct of N,N-dimethyl-acetamide and phosphorus oxychloride according to Example 1 to give 2-(5-nitro-2-furyl)-4-[2-(diethylaminomethyl)-methylene]-hydrazinopyrimidine in the form of red crystals with a melting point of 180° – 182°C.

EXAMPLE 21.

Preparation of 3-(5-Nitro-2-thienyl)-6-[1-formyl-2-(dimethylaminomethylene]-hydrazino-s-triazolo-[4,3-b]pyridazine.

From the cooled dioxan filtrate of the compound prepared in Example 19, there crystallized out 3-(5-nitro-2-thienyl)-6-[1-formyl-2-(dimethylaminomethylene)]-hydrazino-s-triazolo-[4,3-b]-pyrimidazine in the form of red-brown crystals which melted, with decomposition, at 222° – 224°C.

EXAMPLE 22.

Preparation of 2-(5-Nitro-2-furyl)-4-[2-(morpholino)methyl-methylene]-hydrazino-pyrimidine.

2-(5-Nitro-2-furyl)-4-hydrazino-pyrimidine was reacted with the adduct of N-acetyl-morpholine and phosphorus oxychloride in the manner described in Example 1. There was thus obtained, in a yield of 85% of theory, 2-(5-nitro-2-furyl)-4-[2-(morpholinomethyl)-methylene]-hydrazino-pyrimidine in the form of orange-red crystals which, after recrystallization from dioxan, melted at 194° – 197°C.

EXAMPLE 23.

Preparation of 3-(5-Nitro-2-furyl)-6-(dimethylaminomethyleneamino)-s-triazolo-[4,3-b]pyridazine.

0.3 g. 3-(5-nitro-2-furyl)-6-ethoxymethyleneamino-s-triazolo[4,3-b]pyridazole was dissolved in 7 ml. dioxan, mixed at 50°C., while stirring, with 0.23 ml. 40% aqueous dimethylamine solution, stirring continued for 15 minutes, the precipitated product then filtered off with suction, washed with dioxan and recrystallized from 3 ml. dimethyl formamide, 0.22 g. 3-(5-nitro-2-furyl)-6-(dimethylaminomethyleneamino)-s-triazolo-[4,3-b]pyridazine thereby being obtained. This compound had a melting point of 291° – 296°C.

The 3-(5-nitro-2-furyl)-6-ethoxymethyleneamino-s-triazolo[4,3-b]pyridazine used as starting material was prepared in the following manner:

20 g. 3-(5-nitro-2-furyl)-6-amino-s-triazolo[4,3-b]pyridazine were heated with 400 ml. orthoformic acid triethyl ester and 60 ml. acetic anhydric under reflux for 1.5 hours. After cooling, the reaction mixture was diluted with 600 ml. benzene, 400 – 600 ml. ether then added thereto, mixed with activated charcoal, stirred up for some time, then filtered off with suction, thoroughly washed with benzene and the filtrate gently evaporated in a vacuum to a volume of about 250 ml., whereafter the precipitated crystals were filtered off with suction, washed with isopropanol and ether and dried in a vacuum at 80°C. There were thus obtained 12.3 g. 3-(5-nitro-2-furyl)-6-ethoxymethyleneamino-s-triazolo]4,3-b]pyridazine (m.p. 190° – 192°C.). This compound should be stored with the exclusion of air. After recrystallization from a mixture of 70% benzene and 30% dioxan, the compound melted at 193° – 195°C.

EXAMPLE 24.

Preparation of 3-(5-Nitro-2-furyl)-6-dimethylaminomethyleneamino)-s-triazolo[4,3-a]pyridine 0.8 ml. phosphorus oxychloride were added dropwise, with stirring, to 0.7 ml. anhydrous N,N-dimethyl-formamide in 4 ml. anhydrous dioxan at 25° – 30°C., the mixture stirred for a further hour and then 1 g. 3-(5-nitro-2-furyl)-6-amino-s-triazolo[4,3-a]pyridine added thereto. After stirring for 1.5 hours at 30° – 35°C., the reaction mixture was poured on to about 50 g. ice, rendered alkaline at 0°C. with a concentrated aqueous solution of ammonia, the precipitated product filtered off with suction from the weakly alkaline solution and washed with water. After standing for 1 hour, 0.43 g. 3-(5-nitro-2-furyl)-6-(dimethylaminomethyleneamino)-s-triazolo[4,3-a]pyridine precipitate out from the aqueous solution in the form of a black-red precipitate, which was filtered off with suction, washed with water and carefully dried in a vacuum. The product had a melting point of 175° – 178°C.

The following compounds were obtained in an analogous manner from 2-(5-nitro-2-furyl)-4-methyl-6-hydrazino-pyrimidine and the stipulated phosphorus oxychloride adduct:

2-(5-nitro-2-furyl)-4-methyl-6-(dimethylaminomethylene)hydrazino-pyrimidine (m.p. 218° – 222°C.; decomp.) from N,N-dimethyl-formamide-phosphorus oxychloride adduct;

1-methyl-2-[2-(5-nitro-2-furyl)-4-methyl-6-pyrimidinyl]hydrazino-piperidine (m.p. 170° – 172°C.) from N-methyl-2-piperidone-phosphorus oxychloride adduct;

2-(5-nitro-2-furyl)-4-methyl-6-(diethylaminomethylene)hydrazino-pyrimidine (m.p. 209° – 211°C.; decomp.) from N,N-diethyl-formamide-phosphorus oxychloride adduct;

2-(5-nitro-2-furyl)-4-methyl-6-[1-(morpholino)-ethylidene]hydrazino-pyrimidine (m.p. 168° – 170°C.) from N-acetylmorpholine-phosphorus oxychloride adduct.

Furthermore, the following compounds can also be prepared in analogous manner from the stated starting materials:

5-(dimethylaminomethylene)-amino-2-(5-nitro-2-furyl)-pyrimidine (m.p. 209° – 212°C.) from the dimethyl formamide-phosphorus oxychloride adduct and 5-amino-2-(5-nitro-2-furyl)-pyrimidine;

5-(1-dimethylaminoethylidene)-amino-2-(5-nitro-2-furyl)pyrimidine (m.p. 173° – 176°C.) from the dimethyl-acetamidephosphorus oxychloride adduct and 5-amino-2-(5-nitro-2-furyl)pyrimidine;

5-(1-diethylaminoethylidene)-amino-2-(5-nitro-2-furyl)-pyrimidine (m.p. 165° – 168°C.) from the diethyl-acetamide-phosphorus oxychloride adduct and 5-amino-2-(5-nitro-2-furyl)pyrimidine;

5-(diethylaminomethylene)-amino-2-(5-nitro-2-furyl)-pyrimidine (m.p. 153° – 156°C.) from the diethyl formamide-phosphorus oxychloride adduct and 5-amino-2-(5-nitro-2-furyl)-pyrimidine;

5-(morpholino-methylene)-amino-2-(5-nitro-2-furyl)-pyrimidine (m.p. 216° – 218°C.) from the formyl-morpholine-phosphorus oxychloride adduct and 5-amino-2-(5-nitro-2-furyl)-pyrimidine;

5-(1-morpholino-ethylidene)-amino-2-(5-nitro-2-furyl)pyrimidine (m.p. 207° – 211°C.) from the acetyl-morpholine-phosphorus oxychloride adduct and 5-amino-2-(5-nitro-2-furyl)pyrimidine;

1-methyl-2-[2-(5-nitro-2-furyl)-pyrimidinyl-5]-imino-pyrrolidine (m.p. 197° – 199°C.) from the N-methyl-pyrrolidone-(2)phosphorus oxychloride adduct and 5-amino-2-(5-nitro-2-furyl)pyrimidine;

1-methyl-2-[2-(5-nitro-2-furyl)-pyrimidinyl-5]-imino-piperidine (m.p. 158° – 160°C.) from the N-methyl-piperidone-(2)phosphorus oxychloride adduct and 5-amino-2-(5-nitro-2-furyl)pyrimidine;

6-dimethylaminomethylene)-amino-2-methyl-4-(5-nitro-2-furyl)pyrimidine (m.p. 207° – 210°C.) from the dimethyl-formamide-phosphorus oxychloride adduct and 6-amino-2-methyl-4-(5-nitro-2-furyl)-pyrimidine;

6-(diethylaminomethylene)-amino-2-methyl-4-(5-nitro-2-furyl)pyrimidine (m.p. 128° – 130°C.) from the diethyl-formamide-phosphorus oxychloride adduct and 6-amino-2-methyl-4-(5-nitro-2-furyl)-pyrimidine;

1-methyl-2-[2-methyl-4-(5-nitro-2-furyl)-pyrimidinyl-6]-iminopyrrolidine (m.p. 215° – 220°C.) from the N-methyl-pyrrolidone(2)-phosphorus oxychloride adduct and 6-amino-2-methyl-4-(5-nitro-2-furyl)-pyrimidine;

2-(dimethylaminomethylene)-amino-6-chloro-4-(5-nitro-2-furyl)pyrimidine (m.p. 204° – 206°C.) from the dimethyl-formamide-phosphorus oxychloride adduct and 2-amino-6-hydroxy-4-(5-nitro-2-furyl)-pyrimidine;

6-(methyl-2-(morpholino-methylene)-amino-4-(5-nitro-2-furyl)pyrimidine (m.p. 199° – 203°C.) from the formyl-morpholinephosphorus oxychloride adduct and 2-amino-6-methyl-4-(5-nitro-2-furyl)-pyrimidine;

6-(dimethylaminomethylene)-hydrazino-2-methyl-4-(5-nitro-2-furyl)-pyrimidine (m.p. 180° – 181°C.; decomp.) from the dimethyl formamide-phosphorus oxychloride adduct and 6-hydrazino-2-methyl-4-(5-nitro-2-furyl)-pyrimidine;

6-[1-(dimethylaminoethylidene)]-hydrazino-2-methyl-4-(5-nitro-2-furyl)-pyrimidine (m.p. 182° – 184°C.) from the dimethylacetamide-phosphorus oxychloride adduct and 6-hydrazino-2-methyl-4-(5-nitro-2-furyl)-pyrimidine;

6-[1-(diethylaminoethylidene)]-hydrazino-2-methyl-4-(5-nitro-2-furyl)-pyrimidine (m.p. 134° – 136°C.) from the diethylacetamide-phosphorus oxychloride adduct and 6-hydrazino-2-methyl-4-(5-nitro-2-furyl)-pyrimidine;

6-(diethylaminomethylene)-hydrazino-2-methyl-4-(5-nitro-2-furyl)-pyrimidine (m.p. 168° – 170°C.) from the diethylformamide-phosphorus oxychloride adduct and 6-hydrazino-2-methyl-4-(5-nitro-2-furyl)-pyrimidine;

1-methyl-2-[2-methyl-4-(5-nitro-2-furyl)-pyrimidinyl-6]hydrazino-pyrrolidine (m.p. 188° – 190°C.) from the N-methylpyrrolidone-(2)-phosphorus oxychloride adduct and 6-hydrazino-2-methyl-4-(5-nitro-2-furyl)-pyrimidine;

1-methyl-2-[2-methyl-4-(5-nitro-2-furyl)-pyrimidinyl-6]hydrazino-piperidine (m.p. 181° – 183°C.) from the N-methylpiperidone-(2)phosphorus oxychloride adduct and 6-hydrazino-2-methyl-4-(5-nitro-2-furyl)-pyrimidine;

2-methyl-6-(morpholino-methylene)-hydrazino-4-(5-nitro-2-furyl)pyrimidine (m.p. 186° – 191°C.) from the formyl-morpholinephosphorus oxychloride adduct and 6-hydrazino-2-methyl-4-(5-nitro-2-furyl)-pyrimidine;

2-methyl-6-(1-morpholino-ethylidene)-hydrazino-4-(5-nitro-2-furyl)-pyrimidine (m.p. 170° – 172°C.) from the acetyl-morpholinephosphorus oxychloride adduct and 6-hydrozino-2-methyl-4-(5-nitro-2-furyl)-pyrimidine;

5-methyl-3-(morpholino-methylene)-amino-7-(5-nitro-2-furyl)-s-triazolo[4,3-c]pyrimidine (m.p. 240° – 242°C.) from the formylmorpholino-phosphorus oxychloride adduct and 3-amino-5-methyl-7-(5-nitro-2-furyl)-s-triazolo[4,3-c]pyrimidine;

1-methyl-2-[5-methyl-7-(5-nitro-2-furyl)-s-triazolo[4,3-c]pyrimidinyl-3]-imino-pyrrolidine (m.p. 222° – 224°C.) from the N-methyl-pyrrolidone-(2)-phosphorus oxychloride adduct and 3-amino-5-methyl-7-(5-nitro-2-furyl)-s-triazolo[4,3-c]pyrimidine, this latter compound (m.p. 350°C.) being obtained by the reaction of 6-hydrazino-2-methyl-4-(furyl-2)-pyrimidine with cyanobromide to give 3-amino-5-methyl-7-(furyl-2)-s-triazolo[4,3-c]pyrimidine hydrobromide (m.p. 300° – 305°C.) and subsequent nitration;

2,8-dimethyl-5-(dimethylaminomethylene)-amino-7-(5-nitiro-2-furyl)-s-triazolo[2,3-c]pyrimidine (m.p. 237° – 238°C.) from the dimethyl formamide-phosphorus oxychloride adduct and 2,8-dimethyl-5-amino-7-(5-nitro-2-furyl)-s-triazolo[2,3-c]-pyrimidine;

2,8-dimethyl-5-(morpholino-methylene)-amino-7-(5-nitro-2-furyl)-s-triazolo[2,3-c]pyrimidine (m.p. 258° – 260°C.) from the formylmorpholine-phosphorus oxychloride adduct and 2,8-dimethyl-5-amino-7-(5-nitro-2-furyl)-s-triazolo[2,3-c]pyrimidine;

2,8-dimethyl-5-(diethylaminomethylene)-amino-7-(5-nitro-2-furyl)-s-triazolo[2,3-c]pyrimidine (m.p. 213°C.) from the diethylformamide-phosphorus oxychloride adduct and 2,8-dimethyl-5-amino-7-(5-nitro-2-furyl)-s-triazolo[2,3-c]pyrimidine;

1-methyl-2-[2,8-dimethyl-7-(5-nitro-2-furyl)-s-triazolo[2,3-c]pyrimidinyl-5]-imino-piperidine (m.p. 238° – 240°C.) from the N-methyl-piperidone-(2)-phosphorus oxychloride adduct and 2,8-dimethyl-5-amino-7-(5-nitro-2-furyl)-s-triazolo[2,3-c]pyrimidine;

1-methyl-2-[2,8-dimethyl-7-(5-nitro-2-furyl)-s-triazolo[2,3-c]pyrimidinyl-5-]-imino-pyrrolidine (m.p. 244° – 246°C.) from the N-methyl-pyrrolidone-(2)-phosphorus oxychloride adduct and 2,8-dimethyl-5-amino-7-(5-nitro-2-furyl)-s-triazolo[2,3-c]pyrimidine; the latter compound (m.p. 290° – 295°C.) used as starting material was obtained by chlorinating 2-acetamido-4-(2-furyl)-5-methyl-6(1H)-pyrimidinone and the intermediate obtained (m.p. 155° – 160°C.) reacted with hydrazine hydrate to give 2-amino-4-(2-furyl)-6-hydrazino-5-methyl-pyrimidine (m.p. 220° – 222°C.) which was cyclised with orthoacetic acid triethyl ester, the intermediate obtained then nitrated to give 5-amino3,8-dimethyl-7-(5-nitro-2-furyl)-s-triazolo[4,3-c]pyrimidine (m.p. 290°C.; decomp.) which was heated in ethanol saturated with hydrogen chloride;

1-methyl-2-[3,8-dimethyl-7-(5-nitro-2-furyl)-s-triazolo[4,3-c]pyrimidinyl-5]-imino-piperidine (m.p. 258° – 260°C.) from the adduct of N-methyl-piperidone-(2)-phosphorus oxychloride adduct and 3,8-dimethyl-5-amino-7-(5-nitro-2-furyl)-s-triazolo[4,3-c]pyrimidine;

3,8-dimethyl-5-(dimethylaminomethylene)-amino-7-(5-nitro-2-furyl)-s-triazolo-[4,3-c]pyrimidine (m.p. 300° – 304°C.) from the dimethyl formamide-phosphorus oxychloride adduct and 3,8-dimethyl-5-amino-7-(5-nitro-2-furyl)-s-triazolo[4,3-c]pyrimidine;

3,8-dimethyl-5-(morpholino-methylene)amino-7-(5-nitro-2-furyl-s-triazolo[4,3-c]pyrimidine (m.p. 289° – 291°C.; decomp.) from the formyl-morpholine-phosphorus oxychloride adduct and 3.8-dimethyl-5-amino-7-(5-nitro-2-furyl)-s-triazolo[4,3-c]pyrimidine;

3,8-dimethyl-5-(diethylaminomethylene)-amino-7-(5-nitro-2-furyl)-s-triazolo[4,3-c]pyrimidine (m.p. 225°C.) from the diethylformamide-phosphorus oxychloride adduct and 3,8-dimethyl-5-amino-7-(5-nitro-2-furyl)-s-triazolo[4,3-c]pyrimidine.

EXAMPLE 25

Preparation of 3-(5-Nitro-2-furyl)-6-(aminomethyleneamino)-s-triazolo[4,3-b]-pyridazine 0.9 g. 3-(5-nitro-2-furyl)-6-ethoxymethyleneamino-s-triazolo[4,3-b]pyridazine was dissolved in 20 ml. anhydrous dioxan, whereafter gaseous ammonia was passed therethrough for about 5 minutes at 50°C. while stirring was continued for 15 minutes at this temperature, cooled and solid material filtered off the suction. After washing with dioxan, there was obtained 0.77 g. 3-(5-nitro-2-furyl)-6-(aminomethyleneamino)-s-triazolo [4,3-b]-pyridazine. After recrystallization from 35 ml. dimethyl formamide, it was obtained in the form of an intesively yellow powder which melted, with foaming at 269° – 272°C.

EXAMPLE 26.

Preparation of 3-(5-Nitro-2-furyl)-6-(methylaminomethylene)-amino-s-triazolo[4,3-b]pyridazine 0.6 g. 3-(5-nitro-2-furyl)-6-ethoxymethyleneamino-s-triazolo[4,3-b]pyridazine was dissolved in 14 ml. dioxan, mixed at 50°C. with 0.54 ml. 35% aqueous methylamine solution, the reaction mixture stirred at this temperature for a further 15 minutes, the precipitated crystals then filtered off with suction, washed with dioxan and recrystallized from 12 ml. dimethyl formamide. There was thus obtained 0.4 g. 3-(5-nitro-2-furyl)-6-(methylaminomethylene)-amino-s-triazolo[4,3-b]-pyridazine which melted, with foaming, at 289°C.

EXAMPLE 27.

Preparation of 3-(5-nitro-2-furyl)-6-(morpholinomethylene)-amino-s-triazolo[4,3-b]pyridazine.

From 0.95 ml. N-formyl-morpholino and 1 g. 3-(5-nitro-2-furyl)-6-amino-s-triazolo[4,3-b]pyridazine, there was obtained, in a manner analogous to that described in Example 24, 0.97 g. of crude product which, after recrystallization from 16 ml. of a mixture of 80% dioxan and 20% dimethyl formamide, yield 0.43 g. 3-(5-nitro-2-furyl)-6-(morpholino-methylene)-amino-s-triazolo[4,3-b]pyridazine, which had a melting point of 234° – 236°C.

In an analogous manner, there was obtained N-[3-(5-nitro-2-furyl)-6-(-s-triazolo-[4,3-b]pyridazinyl)]-N',-N'-diethyl-acetamidine when diethyl acetamide was used instead of N-formyl-morpholino and the reaction mixture was further stirred for 2 hours at 40° – 45°C. After pouring the reaction mixture on to ice, more than half of the amine used as starting material was recovered as a precipitate and from the filtrate, after rendering it alkaline and leaving to stand overnight, there was obtained N-[3-(5-nitro-2-furyl)-6-(s-triazolo-[4,3-b]pyridazinyl)]-N',N'-diethyl-acetamindine which, after recrystallization from dimethyl formamide-water (1:1), melted at 146° – 147°C.

Furthermore, in an analogous manner, 3-(5-nitro-2-furyl)-6-[1-(1-pyrrolidinyl)-ethylidene]-amino-s-triazolo[4,3,-b]pyridazine was obtained from 2.1 ml. N-acetyl-pyrrolidine and 2 g. 3-(5-nitro-2-furyl)-6-amino-s-triazolo[4,3-b]pyridazine. The yield of crude product was 0.9 g. After recrystallization thereof from 15 ml. dioxan, there was obtained 0.63 g. 3-(5-nitro-2-furyl)-6-[1-(1-pyrrolidinyl)-ethylidene]-amino-s-triazolo[4,3-b]pyridazine, which had a melting point of 209° – 211°C.

Also in an analogous manner, 3-(5-nitro-2-furyl)-6-[1-(morpholino)-ethylidene]-amino-s-triazolo[4,3-b]pyridazine was obtained from 2.1 ml. N-acetyl-morpholino and 2 g. 3-(5-nitro-2-furyl)-6-amino-triazolo[4,3-b]pyridazine at a reaction temperature of 40° – 45°C. After recrystallization from a mixture of 90% dioxan and 10% dimethyl formamide, the product had a melting point of 237° – 246°C.

Yet again in an analogous manner, from 1.9 g. N-formyl piperidine and 2 g. 3-(5-nitro-2-furyl)-6-amino-triazolo[4,3-b]pyridazine, there was obtained 3-(5-nitro-2-furyl)-6-(piperidine methyleneamino)-s-triazolo[4,3-b]pyridazine which, after recrystallization from 70% aqueous dimethyl formamide, had a melting point of 202° – 203°C.

EXAMPLE 28.

Preparation of 3-(5-nitro-2-furyl)-6-(4-methyl-1-piperazinylmethyleneamino)-s-triazolo[4,3-b]pyridazine.

0.9 g. 3-(5-nitro-2-furyl)-6-(ethyoxymethyleneamino)-s-triazolo[4,3-b]pyridazine were dissolved in 20 ml. hot dioxan and mixed, while stirring, with 0.6 g. N-methyl-piperazine at 50°C. After 15 minutes, the crystals formed were filtered off with suction and recrystallized from 15 ml. of a mixture of 70% dioxan and 30 ml. dimethyl formamide. There was thus obtained 0.77 g. 3-(5-nitro-2-furyl)-6-(4-methyl-1-piperazinyl methyleneamino)-s-triazolo[4,3-b]pyridazine, which had a melting point of 247° – 248°C.

EXAMPLE 29.

Preparation of 3-(5-nitro-2-furyl)-6-methyl-7-(or -5-)(dimethylaminomethylene)-amino-s-triazolo [4,3-a]pyrimidine.

0.35 g. 3-(5-nitro-2-furyl)-6-methyl-7-(or-5-)amino-s-triazolo[4,3-a]pyrimidine was dissolved in 8 ml. hot dimethyl formamide, then mixed with 0.41 ml. N,N-dimethyl formamide diethyl acetal, whereafter the reaction mixture was dipped into a bath with a temperature of 100°C., stirring continued for 2 hours at 100°C., the crystals which precipitated were filtered off with suction, washed with dimethyl formamide and with ether, there was thus being obtained 0.27 g. 3-(5-nitro- 2-furyl)-6-methyl-7-(or-5-)-(dimethylaminomethylene)-amino-s-triazolo-[4,3-a]pyrimidine, which had a melting point of 292° – 294°C.

The 3-(5-nitro-2-furyl)-6-methyl-7-(or-5-)amino-s-triazolo[4,3-a]pyrimidine used as starting material, was prepared in the following manner:

6.8 g. crude 2-hydrazino-4-amino-5-methyl-pyrimidine (m.p. 174° – 175°C.), which was prepared by treating 8 g. 2-chloro-4-methyl-pyrimidine with 40 ml. hydrazine hydrate for 1.5 hours at 100°C., were dissolved in a mixture of 79 ml. water and 37 ml. 2N hydrochloric acid, a solution of 8.3 g. 5-nitro-furan-2-aldehyde in 116 ml. methanol then added thereto, the reaction mixture left to stand for 1 hour at ambient temperature and the precipitated crystals filtered off with suction, washed with 50% aqueous methanol and then with ether, there thus being obtained 12.7 g. of the crude hydrazone, which had a melting point of 264° – 268°C.

This hydrazone was then suspended in 212 ml. glacial acetic acid and, while stirring 27.8 g. lead tetraacetate introduced into the suspension, the temperature thereby increasing to 40°C. The reaction mixture was further stirred for 1 hour at ambient temperature, subsequently evaporated in a vacuum, 150 ml. water added to the evaporation residue, the pH adjusted to about 8 with ammonia and undissolved material filtered off with suction. After washing with water and drying, there were obtained 9.1 g. crude 3-(5-nitro-2-furyl)-6-methyl-5-(or-7-)amino-s-triazolo[4,3-a]pyrimidine, which melted, with foaming, at 258° – 260°C.

EXAMPLE 30.

Preparation of 3-(5-nitro-2-furyl)-6-(1-dimethylaminoethylidene)-hydrazino-s-triazolo[4,3-b]-pyridazine.

1.6 ml. phosphorus oxychloride were added portionwise at 35° – 40°C. to 1.6 ml. dimethyl acetamide in 7 ml. anhydrous dioxan, the reaction mixture was then stirred for 1 hour at this temperature, 2 g. 3-(5-nitro-2-furyl)-6-hydrazino-s-triazolo [4,3-b]pyridazine added thereto and the reaction mixture then further stirred for 1.5 hours at 35° – 40°C., whereafter it was poured on to 100 g. crushed ice, left to stand for some time, insoluble material was filtered off with suction, the filtrate was rendered alkaline by the addition of a slight excess of concentrated aqueous ammonia solution, the precipitated material was filtered off with suction, washed with water and recrylstallized from 15 ml. dimethyl formamide, with the adition of activated charcoal. There was thus obtained 0.53 g. 3-(5-nitro-2-furyl)-6-(1-dimethylaminoethylidene) hydrazino-s-triazolo [4,3-b]pyridazine in the form of a dark red powder which melted, with foaming, at 269° – 270°C.

In an analogous manner, from 1.7 ml. N-methyl-pyrrolidone-(2) and 2 g. 3-(5-nitro-2-furyl)-6-hydrazino-s-triazolo[4,3-b]pyridazine, there was obtained 1.13 g. of crude product which, after recrystallization from 14 ml. of a mixture of dimethyl formamide and dioxan (1:1), gave 0.75 g. of red-brown 1-methyl-2-[3-(5-nitro-2-furyl)-6-(s-triazolo[4,3-b]pyridazinyl)]hydrazino-pyrrolidine which melted, with foaming, at 247° – 249°C.

Also in an analogous manner, from 1.9 ml. N-methyl-2-piperidone and 2 g. 3-(5-nitro-2-furyl)-6-hydrazino-s-triazolo[4,3-b]pyridazine, there was obtained 1.6 g. crude product which, after recrystallization from 18 ml. 80% aqueous dimethyl formamide yields 0.73 g. of dark red 1-methyl-2-[3-(5-nitro-2-furyl)-6-(s-triazolo[4,3-b]pyridazinyl)]-hydrazino-piperidine which melted, with foaming at 236° – 238°C.

EXAMPLE 31.

Preparation of 1-Methyl-2-[3-(5-nitro-2-furyl)-5-(1,2,4-thiadiazolyl)]-imino-pyrrolidine.

From 0.85 ml. N-methyl-2-pyrrolidone and 0.8 ml. phosphorus oxychloride in 4 ml. dioxan, there was prepared, in a manner analogous to that described in Example 24, a dioxan solution of the adduct to which was added 1 g. 3-(5-nitro-2-furyl)-5-amino-1,2,4-thiadiazole, whereafter the reaction mixture was stirred for 1.5 hours at 35° – 40°C. The reaction mixture was now poured on to 50 g. crushed ice, rendered weakly alkaline with a concentrated aqueous solution of ammonia, the precipitated material was filtered off with suction, washed with water and recrystallized from 10 ml. dioxan, with the addition of activated charcoal. There was thus obtained 0.68 g. 1-methyl-2-[3-(5-nitro-2-furyl)-5-(1,2,4-thiadiazolyl)]-imino-pyrrolidine, which had a melting point of 193° – 196°C.

The 3-(5-nitro-2-furyl)-5-amino-1,2,4-thiadiazole used as starting material was prepared in the following manner:

32.7 g. crude 5-nitro-2-furamidine hydrochloride (m.p. 232° – 234°C.) were suspended in 910 ml. anhydrous acetone, 32 g. trichloromethyl-sulfenyl chloride added thereto, while stirring, followed by the dropwise addition of 91 ml. triethylamine at 0° – 5°C. and in the course of 20 minutes, followed by stirring at this temperature for 40 minutes and then at 50° – 55°C. for 2 hours. After cooling, precipitated triethylamine hydrochloride was filtered off with suction, the filtrate was evaporated in a vacuum, the evaporation residue was triturated with water, the pH adjusted to about 5 with sodium acetate, undissolved material was filtered off with suction, the still moist material was triturated with methanol, filtered with suction, then washed with methanol and dried in a vacuum at 80°C.; there was obtained 17.5 g. crude 3-(5-nitro-2-furyl)-4-chloro-1,2,5-thiadiazole, which had a melting point of 160° – 162°C. After recrystallization from methanol-dioxan (1:1), with the use of activated charcoal, the compound had a melting point of 167° – 168°C.

13.8 of the crude product thus obtained were dissolved in a mixture of 500 ml. ethanol and 150 ml. dioxan, gaseous ammonia passed therein for 4 hours at 70°C., while stirring, the solution then mixed with activated charcoal, suction filtered while still hot, the clear filtrate concentrated in a vacuum to about 70 ml., the precipitated crystals filtered off with suction, washed with ethanol, water and, finally, with ether, there thus being obtained 7.5 g. crude 3-(5-nitro-2-furyl)-5-amino-1,2,4-thiadiazole which melted, with decomposition, at 277° – 278°C.

In an analogous manner, from 0.8 ml. N,N-dimethylacetamide and 1 g. 3-(5-nitro-2-furyl)-5-amino-1,2,4-thiadiazole there was obtained 1.06 g. of crude product which, after recrystallization from 8 ml. 70% aqueous dioxan, yield 0.5 g. 3-(5-nitro-2-furyl)-5-(1-dimethylaminoethylidene)-amino-1,2,4-thiadiazole which had a melting point of 168° – 170°C.

Also in an analogous manner, from 0.95 ml. N-formylmorpholino and 1 g. 3-(5-nitro-2-furyl)-5-amino-1,2,4-thiadiazole, there was obtained 1.37 g. of crude product which, after recrystallization from 10 ml. dioxan, yield 1.05 g. 3-(5-nitro-2-furyl)-5-(morpholinomethylene)-amino-1,2,4-thiadiazole which had a melting point of 204° – 205°C.

EXAMPLE 32.

Preparation of
3-(5-nitro-2-furyl)-5-(methylaminomethylene)-amino-1,2,4-thiadiazole.

0.54 g. crude 3-(5-nitro-2-furyl)-5-ethoxymethyleneamino-1,2,4-thiadiazole was dissolved in 10 ml. of a hot mixture of dioxan-benzene (1:1), mixed at 10°C., while stirring, with 0.55 ml. of an 18% methanolic solution of methylamine, further stirred for 15 minutes at this temperature, undissolved material filtered off with suction, washed with dioxan and then with ether, there thus being obtained 0.37 g. 3-(5-nitro-2-furyl)-5-(methylaminomethylene)-amino-1,2,4-thiadiazole which melted at 196° – 198°C.

The 3-(5-nitro-2-furyl)-5-ethoxymethyleneamino-1,2,4-thiadiazole used as starting material was prepared in the following manner:

6.5 g. 3-(5-nitro-2-furyl)-5-amino-1,2,4-thiadiazole were boiled under reflux for 1.5 hours with 80 ml. orthoformic acid triethyl ester, the reaction mixture then diluted with 100 ml. benzene, activated charcoal added thereto, again boiled up, filtered with suction and the filtrate carefully evaporated in a vacuum. The evaporation residue was triturated with 25 ml. isopropanol, filtered with suction, washed with ether and dried to give 5.4 g. of the desired product in the form of a crude material (m.p. 126° – 140°C.) which was further reacted as such.

In an analogous manner, from 0.54 g. 3-(5-nitro-2-furyl)-5-ethoxymethyleneamino-1,2,4-thiadiazole and 15 ml. of a dioxan-benzene mixture (1:1), by passing through gaseous ammonia for 10 minutes at 10°C., further stirring for 15 minutes and then working up the reaction mixture, there was obtained 0.3 g. 3-(5-nitro-2-furyl)-5-(aminomethylene)-amino-1,2,4-thiadiazole which melted, with foaming, at 204° – 208°C.

EXAMPLE 33.

Preparation of
4-(5-Nitro-2-furyl)-2-(dimethylaminomethylene)-amino-thiazole.

In a manner analogous to that described in Example 24, there was obtained, at 35° – 40°C., from 1.7 g. 4-(5-nitro-2-furyl)-2-amino-thiazole and 1.35 ml. N,N-dimethyl-formamide, 1.94 g. crude product, 10 ml. concentrated aqueous ammonia solution having been added to the ice before pouring on the reaction mixture. After recrystallization of the product from 25 ml. benzene, there was obtained 1.18 g. 4-(5-nitro-2-furyl)-2-(dimethylaminomethylene)-amino-thiazole, which had a melting point of 178° – 179°C.

In an analogous manner, from 1.9 ml. N-methyl-piperidone-2 and 2 g. 4-(5-nitro-2-furyl)-2-amino-thiazole, at a reaction temperature of 40° – 45°C., there were obtained 2.1 g. of crude product which, after recrystallization from 32 ml. isopropanol, yield 1.27 g. 1-methyl-2-[4-(5-nitro-2-furyl)-2-thiazolyl]imino-piperidine, which had a melting point of 142° – 144°C.

EXAMPLE 34.

Preparation of
3-(5-Nitro-2-furyl)-5-(dimethylaminomethylene)-amino-1,2,4-oxadiazole.

0.56 ml. N,N-dimethyl-formamide in 2.8 ml. anhydrous dioxan was mixed with 0.64 ml. phosphorus oxychloride, the reaction mixture was stirred for 1 hour at 25° – 30°C., 0.8 g. crude 3-(5-nitro-2-furyl)-5-amino-1,2,4-oxadiazole (m.p. 210°C.) added thereto, the reaction mixture stirred for 1.5 hours at 25° – 30°C., then poured on to 10 ml. crushed ice, rendered alkaline to pH of 8 with a concentrated aqueous solution of ammonia, undissolved material filtered off with suction and then recrystallized from 25 ml. 80% aqueous dioxan. There was obtained 0.55 g. 3-(5-nitro-2-furyl)-5-(dimethylaminomethylene)-amino-1,2,4-oxadiazole, which had a melting point of 208° – 210°C.

EXAMPLE 35.

Preparation of
1-Methyl.-2-[3-nitro-2-furyl)-5-(1,2,4-thiadiazolyl]-hydrazino-pyrrolidine.

In a manner analogous to that described in Example 24, from 1.7 ml. N-methyl-pyrrolidone-2 and 2 g. 3-(5-nitro-2-furyl)-5 -hydrazino-1,2,4-thiadiazole in 7 ml. dioxan at a temperature of 35° – 40°C., there were obtained 2.37 g. crude product from which, after recrystallization from 12 ml. dioxan with the addition of activated charcoal, there was obtained 1.64 g. dark-red 1-methyl-2-[3-(5-nitro-2-furyl)-5-(1,2,4-thiadiazolyl)]-hydrazino-pyrrolidine which melted, with foaming, at 200°C.

The 3- (5-nitro-2-furyl)-5-hydrazino-1,3,4-thiadiazole used as starting material was prepared in the following manner:

7 g. 3-(5-nitro-2-furyl)-5-chloro-1,2,4-thiadiazole (m.p.160° – 162°C.) were dissolved in a mixture of 106 ml. dioxan and 45 ml. isopropanol, 3 ml. hydrazine hydrate were added thereto dropwise at 35° – 40°C., while stirring, whereafter stirring was continued for 15 minutes, undissolved material was filtered off with suction, which then was washed with water and dioxan and dried, there being obtained 4,29 g. 3-(5-nitro-2-furyl)-5-hydrazino-1,3,4-thiadiazole, which melted, with foaming, at 214° – 217°C.

EXAMPLE 36

Preparation of
2-(5-nitro-2-furyl)-4-methylmercapto-6-(dimethylaminomethylene)-amino-s-triazine.

In a manner analogous to that described in Example 24, from 1.33 ml. N,N-dimethyl-formamide, 1.6 ml. phosphorus oxychloride, 7 ml. dioxan and 2 g. 2-(5-nitro-2-furyl)-4-methylmercapto-6-amino-s-triazine, there was obtained 1.45 g. crude product, whereby it was weakly alkalized with a concentrated aqueous solution of ammonia. Recrystallization of the crude product from 21 ml. of a mixture of benzene and dioxan (2:1) yield 0.81 g. 2-(5-nitro-2-furyl)-4-methylmercapto-6-(dimethylaminomethylene)-amino-s-triazine, which had a melting point of 179° – 181°C.

The 2-(5-nitro-2-furyl)-4-methylmercapto-6-amino-s-triazine used as starting material was synthesized in the following manner:

From thiocarbamoyl-guanidine, there was prepared, by means of dimethyl sulfate, the methosulfate of the s-methyl compound and 5.46 g. of the crude material suspended in 24 ml. benzene. At a temperature, of 5° – 10°C., there was introduced, with stirring, a solution of 3.51 g. 5-nitrofuran-2-carboxylic acid chloride in 10 ml. benzene within the course of 15 minutes, stirring thereafter being continued at this temperature for 30 minutes, whereafter 4.52 g. triethylamine were added dropwise, with stirring, at 5° – 10°C., stirring being continued for 2 hours at ambient temperature and then for a further 2 hours at 40° – 45° C. The reaction mixture then mixed with 45 ml. water, stirred for 15 minutes at ambient temperature, undissolved material was filtered off with suction, washed with water and the still moist material recrystallized from a mixture of dioxan-methanol (6:4), with the addition of activated charcoal. There was thus obtained 1.15 g. 2-(5-nitro-2-furyl)-4-methylmercapto-6-amino-s -triazine, which had a melting point of 252° – 254°C.

EXAMPLE 37

Preparation of
5-(5-nitro-2-furyl)-3-(dimethylaminomethylene)-amino-s-triazolo-[4,3-d]-thiadiazole-(1,2,4).

In a manner analogous to that described in Example 24, from 0.7 ml. N,N-dimethyl-formamide, 1 g. 5-(5-nitro-2-furyl)-3-amino-s-triazolo[4,3-d]thiadiazole-(1,2,4), 4 ml. dioxan and 0.8 ml. phosphorus oxychloride, there was obtained, after pouring the reaction mixture on to ice and rendering alkaline with a concentrated aqueous solution of ammonia, 1.04 g. of crude product from which, after recrystallization from 16 ml. of a mixture of 80% dimethyl formamide and 20% dioxan, there was obtained 0.4 g. 5-(5-nitro-2-furyl)-3-(dimethylaminomethylene)-amino-s-triazolo[4,3-d]-thiadiazole-(1,2,4), which had a melting point of 248° – 250°C.

The 5-(5-nitro-2-furyl)-3-amino-s-triazolo[4,3-d]thiadiazole-(1,2,4) used as starting material was prepared in the following manner:

1.1 g. 3-(5-nitro-2-furyl)-5-hydrazino-1,2,4-thiadiazole was boiled under reflux with 35 ml. methanol and 0.7 g. cyanobromide for 1.5 hours, whereafter two further amounts of 0.7 g. cyanobromide were added, reflux boiling for 1.5 hours being continued after each addition. After cooling the reaction mixture, solid material was filtered off with suction. The filter residue was triturated with water, the pH adjusted to 5, again filtered off with suction, washed with water and dried. There was thus obtained 0.43 g. 5-(5-nitro-2-furyl)-3-amino-s-triazolo[4,3-d]thiadiazole-(1,2,4) in the form of a red powder which melted, with foaming, at 198° – 199°C.

In an anlogous manner, there was obtained, 5-(5-nitro-2-furyl)-3-(dimethylaminomethylene)-amino-s-triazolo[3,4-b]thiazole from 1 ml. anhydrous N,N-dimethyl-formamide, 5 ml. dioxan, 1.2 ml. phosphorus oxychloride and 1.5 g. 5-(5-nitro-2-furyl)-3-amino-s-triazolo[3,4-b]thiazole: there was first obtained 1.7 g. of crude product which, after recrystallization from 14 ml. dimethyl formamide, yield 1 g. red-brown 5-(5-nitro-2-furyl)-3-(dimethylaminomethylene)-amino-s-triazolo[3,4-b]thiazole which melted, with decomposition, at 270° – 272°C.

The 5-(5-nitro-2-furyl)-3-amino-s-triazolo[3,4-b]thiazole used as starting material was prepared in the following manner:

1.35 g. 3-(5-nitro-2-furyl)-2-hydrazino-thiazole was suspended in 30 ml. methanol, boiled under reflux for 1.5 hours with 0.9 g. cyanobromide dissoved in 15 ml. methanol, the small amount of insoluble material filtered off with suction, the filtrate evaporated in a vacuum, the evaporation residue triturated with water, the pH adjusted to 6, insoluble material filtered off with suction and recrystallized from 15 ml. of a mixture of 70% dimethyl formamide and 30% dioxan, with the addition of activated charcoal, to give 0.42 g. black-red crystals of 5-(5-nitro-2-furyl)-3-amino-s-triazolo[3,4-b]thiazole, which melted at 238°C.

EXAMPLE 38.

Preparation of
1-Methyl-2-[6-(5-nitro-2-furyl)-3-(s-triazolo[3,4-b]1,3,4-thiadiazolyl)]-iminopyrrolidine.

1.2 ml. N-methyl-pyrrolidone in 3.5 ml. anhydrous dioxan were mixed with 1 ml. phosphorous oxychloride, the reaction mixture stirred for 1 hour at 25° – 30°C., 1 g. 6-(5-nitro-2-furyl)-3-amino-s-triazolo[3,4-b]thiadiazole-(1,3,4) added thereto, the reaction mixture further stirred for 1.5 hours at 25° – 30°C., poured into 30 ml. ice water, the pH adjusted to 8 with ammonia, the precipitated product filtered off with suction, washed with water and dried to give 1 g. of crude product which, after recrystallization from 60 ml. of a mixture of dioxan and dimethyl formamide (9:1), gave 0.25 g. of starting material. The mother liquor was evaporated in a vacuum and the evaporation residue was boiled out with 60 ml. isopropanol, 0.1 g. 1-methyl-2-[6-(5-nitro-2-furyl)-3-(s-triazolo[3,4-b]1,3,4-thiadiazolyl)]-imino-pyrrolidine remained behind undissolved. A further 0.3 g. of the end product can be obtained from the cooled isopropanol solution. The product had a melting point of 222° – 225°C.

EXAMPLE 39.

Preparation of
2-(5-Nitro-2-furyl)-4-(morpholinomethylene)-hydrazino-pyrimidine.

2-(5-Nitro-2-furyl)-4-hydrazino-pyrimidine was reacted, in a manner analogous to that described in Example 24, with the adduct -pyrrolidinyl)-ethylidene]-from N-formyl-morpholino and phosphorus oxychloride to give 2-(nitro-2-furyl)-4-(morpholinomethylene)-hydrazino-pyrimidine in the form of dark red crystals which, after recrystallization from aqueous dioxan, melted, with decomposition, at 229°C.

In an analogous manner, from N-acetyl-pyrrolidine and phosphorus oxychloride adduct, there was obtained 2-(5-nitro-2-furyl)-4-]1-(1-pyrrolidinyl)-ethylene]-hydrazino-pyrimidine which melted, with bubbling, at 232° – 234°C.

EXAMPLE 40.

Preparation of
2-(5-nitro-2-furyl)-4-(dimethylaminomethylene)-amino-pyrimidine.

Variant A.

2-(5-Nitro-2-furyl)-4-amino-pyrimidine was reacted, in a manner analogous to that described in Example 24, with the adduct of dimethyl formamide and phosphorus oxychloride. There was obtained paper-chromatographically pure 2-(5-nitro-2-furyl)-4-(dimethylaminomethylene)-amino-pyrimidine in the form of yellow crystals which, after recrystallization from dioxan, melted at 194° – 197°C.

Variant B.

2-(2-Furyl)-4-amino-pyrimidine was reacted with N,N-dimethyl formamide diethyl acetal to give the corresponding amidine (m.p. 100°–103°C.), which was nitrated in acetic anhydride solution at –10°C. with a mixture of concentrated sulfuric acid and 100% nitric acid. Subsequently, the reaction mixture was poured on to ice, the clear solution obtained was neutralized with ammonia and the precipitated crystals were filtered off with suction. After recrystallization from dioxan, with the addition of activated charcoal, there were obtained yellow crystals with a melting point of 195° – 198°C. A mixed melting point with the product obtained according to the above Variant A shows no depression.

In a manner analogous to that described in the above Variant B but with the use of the adduct of N,N-diethyl formamide and phosphorus oxychloride, there was obtained 2-(5-nitro-2-furyl)-4-(diethylaminomethylene)-amino-pyrimidine which, after recrystallization from methanol, had a melting point of 135° – 138°C.

EXAMPLE 41.

Preparation of 2-(Dimethylaminoethylene)-amino-4-(5-nitro-2-furyl)-6-ethoxy-pyrimidine.

2-Amino-4-(5-nitro-2-furyl)-6-hydroxy-pyrimidine was reacted, in a manner analogous to that described in Variant A of Example 12, with N,N-dimethyl formamide diethyl acetal. There was thus obtained 2-(dimethylaminomethylene)-amino-4-(5-nitro-2-furyl)-6-ethoxy-pyrimidine in the form of yellow crystals which have a melting point of 171° –173°C.

EXAMPLE 42.

Preparation of 3-(5-Nitro-2-furyl)-6-dimethylaminomethylene)-amino-pyridazine.

0.8 g. 3-(5-nitro-2-furyl)-6-aminopyridazine in 2.4 ml. dioxan were reacted, in a manner analogous to that described in Example 24, with 0.63 ml. dimethyl formamide and 0.74 ml. phosphorus oxychloride in 3,3 ml dioxan. In this way, there was obtained 0.9 g. (88% of theory) 3-(5-nitro-2-furyl)-6-(dimethylaminomethylene)-amino-pyridazine in the form of paper chromatographically uniform, yellow crystals which melted at 222° – 224°C.

The 3-(5-nitro-2-furyl)-6-amino-pyridazine used as starting material was prepared in the following manner:

4,5-dihydro-3-(2-furyl)-6-(1H)-pyridazinone (see J. Med. Chem.,9, 425/1966) was dehydrated by treatment with an oxidation agent and the 3-(2-furyl)-6-(1H)-pyridazinone (m.p. 183° – 184°C.) obtained was reacted with phosphorus oxychloride. The 3-(2-furyl)-6-chloropyridazine (m.p. 103° – 104°C.) obtained was reacted with aqueous ammonia in an autoclave at 140°C. to give the corresponding amino compound (m.p. 223° – 226°C.) which was, in turn, acetylated with acetic anhydride in the presence of pyridine. The resultant 3-(2-furyl)-6-acetamino-pyridazine (m.p. 257° – 258°C.) was nitratedin concentrated sulfuric acid in the usual way. After working up the reaction mixture, there was obtained a product which, after recrystallization from dimethyl formamide, melted, with decomposition, at 300° – 305°C. It was subsequently deacetylated by heating with dilute hydrochloric acid to give 3-(5-nitro-2-furyl)-6-amino-pyridazine which melted, with decomposition, at 268°C.

EXAMPLE 43.

Preparation of 3-(dimethylaminomethylene)-amino-6-(5-nitro-2-furyl)-s-triazolo[4,3-b]pyridazine.

3 g. 3-(dimethylaminomethylene)-amino-6-(2-furyl)-s-triazolo[4,3-b]pyridazine were suspended in 30 ml. acetic anhydride and nitrated in the usual manner at –10°C. with a mixture of nitric acid and sulfuric acid. After subsequently stirring the reaction mixture for one hour, it was poured on to ice, the clear solution obtained was neutralized with ammonia, the precipitated crystals were filtered off with suction, washed with water and recrystallized from methanol, with the addition of dimethyl formamide. There was obtained 0.6 g. 3-(dimethylaminomethylene)-amino-6-(5-nitro-2-furyl)-s-triazolo[4,3-b]pyridazine in the form of red crystals which had a melting point of 249° – 252°C.

The 3-(dimethylaminomethylene)-amino-6-(2-furyl)-s-triazolo[4,3-b]pyridazine used as starting material was prepared in the following manner:

3-(2-furyl)-6-chloropyridazine was boiled for 4 hours with excess hydrazine hydrate in isopropanol, the reaction mixture was then evaporated in a vacuum and the crystalline residue stirred up with water and recrystallized from water. The hydrazine compound (m.p. 171° – 173°C.) thus obtained was now cyclised with cyanobromide in methanol to give 3-amino-6-(2-furyl)-s-triazolo[4,3-b]pyridazine, which, after recrystallization from methanol, with the addition of some dimethyl formamide, melted at 244° – 247°C. This compound was then reacted, in a manner analogous to that described in Example 24, with the adduct of dimethyl formamide and phosphorus oxychloride to give, finally, the desired 3-(dimethylaminomethylene)-amino-6-(2-furyl)-s-triazolo[4,3-b]pyridazine which, after recrystallization from alcohol, was obtained in the form of yellow crystals which melted at 203° – 206°C.

EXAMPLE 44.

Preparation of 6-(5-Nitro-2-furyl)-2-(dimethylaminomethylene)-amino-imidazo-[2,1-b]-1,3,4-thiadiazole.

In a manner analogous to that described in Example 24, from 1.4 ml. N,N-dimethyl formamide, 7 ml. dioxan and 1.6 ml. phosphorus oxychloride, as well as 2 g 6-(5-nitro-2-furyl)-2-amino-imidazo[2,1-b]-1,3,4-thiadiazole, there was obtained, at 30° – 35°C., a thick crystal slurry which could no longer be stirred. This was poured on to 100 g. crushed ice and rendered slightly alkaline with ammonia. There was obtained 2.46 g. of crude product which, after recrystallization from 16 ml. dimethyl formamide, gives 1.53 g. 6-(5-nitro-2-furyl)-2-(dimethylaminomethylene)-amino-imidazo[2,1-b]-1,3,4-thiadiazole which had a melting point of 257° – 258°C.

The 6-(5-nitro-2-furyl)-2-amino-imidazo[2.1-b]-1,3,4-thiadiazole used as starting material was prepared in the following manner:

1.16 g. 2,5-diamino-1,3,4-thiadiazole, dissolved in 40 ml. hot ethanol, was mixed with a solution of 2.34 g. 5-nitro-2-bromoacetyl-furan in 10 ml. ethanol. Thereafter, the reaction mixture was boiled under reflux for 1 hour, cooled, the precipitated crude crystals were filtered off with suction, washed with alcohol and dried in a vacuum at 60°C. The yield was 2.28 g. and the product melted, with foaming, at 247° – 250°C.

1 g. 2-amino-4-(5-nitro-2-furyl)-methyl-5-imino-1,3,4-thiadiazole hydrobromide was broiled under reflux for 3.5 hours in 20 ml. water, cooled, the crystals obtained filtered off with suction and recrystallized from 9 ml. 90% aqueous dimethyl formamide, the desired compound being obtained in a yield of 0.3 g. It had a melting point of 304°C.

EXAMPLE 45.

Preparation of
3-(5-Nitro-2-furyl)-6-(2-methyl-5-pyrimidinylamino-methylene)-amino-s-triazolo[4,3-b]pyridazine.

0.9 g. 3-(5-nitro-2-furyl)-6-(ethoxy-methylene)-amino-s-triazolo[4,3-b]pyridazine was dissolved in 18 ml. dioxan, mixed at 50° – 60°C., while stirring, with 0.48 g. 2-methyl-5-amino-pyrimidine, stirring continued for 15 minutes, the precipitated product filtered off with suction, washed with dioxan and recrystallized from 20 ml. dimethyl formamide. There were obtained 55 g. 3-(5-nitro-2-furyl)-6-(2-methyl-5-pyrimidinylamino-methylene)amino-s-triazolo[4,3-b]pyridazine which had a melting point of 292° – 294°C.

In an analogous manner, from 0.6 g. 3-(5-nitro-2-furyl)-6-(ethoxy-methylene)-amino-s-triazolo[4,3-b]pyridazine in 12 ml. anhydrous dioxan and an ethanolic solution of hydroxylamine (prepared from 0.6 g. hydroxylamine hydrochloride in 15 ml. absolute ethanol by adding 0.14 g. sodium, dissolved in 5 ml. absolute ethanol, and filtering off with suction the precipitated sodium chloride) at 50° – 60°C., there was obtained, after a reaction period of 15 minutes and cooling of the reaction mixture, 0.55 g. 3-(5-nitro-2-furyl)-6-(hydroxylaminomethylene)-amino-s-triazolo[4,3-b]pyridazine, which melted, with foaming, at 251° – 253°C.

EXAMPLE 46.

Preparation of
3-(5-Nitro-2-furyl)-6-[(N-β-hydroxyethyl-N-methylamino)-methylene]-amino-s-triazolo[4,3-b]pyridazine.

0.9 g. crude 3-(5-nitro-2-furyl)-6-ethoxymethyleneamino-s-triazolo[4,3-b]pyridazine was dissolved in 20 ml. dioxan, mixed at 50°C., while stirring, with 0.45 ml. N-methyl-N-3-hydroxyethylamine, stirring continued for 15 minutes at 50°C., the reaction mixture cooled, solid material filtered off with suction, washed with dioxan and recrystallized from 13 ml. of a mixture of 80% dioxan and 20% dimethyl formamide, there being obtained 0.52 g. 3-(5-nitro-2-furyl)-6-[(N-β-hydroxyethyl-N-methylamino)-methylene]-amino-s-triazolo[4,3-b]pyridazine which had a melting point of 205° – 208°C.

In an analogous manner, from 0.9 g. 3-(5-nitro-2-furyl)-6-ethoxymethyleneamino-s-triazolo[4,3-b]pyridazine and 0.65 ml. N,N-di-β-hydroxyethylamine, there was obtained 1.02 g. of crude product from which, by recrystallization, there was obtained 0.75 g. 3-(5-nitro-2-furyl)-6-[(N,N-di-β-hydroxyethylamino)-methylene]-amino-s-triazolo[4,3-b]pyridazine which melted, with decomposition, at 175° – 177°C.

In an analogous manner, from 0.6 g. 3-(5-nitro-2-furyl)-6-ethoxymethyleneamino-s-triazolo[4,3-b]pyridazine and N,N-dimethyl-hydrazine in 14 ml. dioxan, there was obtained 0.53 g. of crude product from which, after recrystallization from 11 ml. dimethyl formamide, there was obtained 0.41 g. 3-(5-nitro-2-furyl)-6-[(2-N,N-dimethylhydrazino)-methylene]-amino-s-triazolo[4,3-b]pyridazine which melted, with foaming, at 265° – 267°C.

Again in an analogous manner, from 1.5 g. 3-(5-nitro-2-furyl)-6-ethoxymethyleneamino-s-triazolo[4,3-b]pyridazine in 25 ml. dioxan and reaction with 1.2 ml. N-methyl-aniline, there was obtained, after a reaction time of 30 minutes at 50° – 60°C., 0.57 g. 3-(5-nitro-2-furyl)-6-(N-methyl-N-phenylaminomethylene)-amino-s-triazolo[4,3-b]pyridazine which had a melting point of 233° – 236°C., a change taking place at 225°C.

yet again in an analogous manner from 0.6 g. 3-(5-nitro-2-furyl)-6-ethoxymethyleneamino-s-triazolo[4,3-b]pyridazine in 12 ml. dioxan and 0.28 g. p-aminophenol, there was obtained, after a reaction time of 15 minutes at 50° – 60°C., 0.44 g. 3-(5-nitro-2-furyl)-6-(N-p-hydroxyphenylaminomethylene)-amino-s-triazolo[4,3-b]pyridazine which melted, with foaming, at 266° – 268°C.

Also in an analogous manner, from 0.9 g. 3-(5-nitro-2-furyl)-6-ethoxymethylamino-s-triazolo[4,3-b]pyridazine in 18 ml. dioxan and 0.75 g. p-methoxy-aniline, there was obtained after a reaction time of 15 minutes at 50° – 60°C., 0.86 g. of crude product which, after recrystallization from dimethyl formamide, gives 0.7 g. 3-(5-nitro-2-furyl)-6-(N-p-methoxyphenylaminomethylene)-amino-s-triazolo[4,3-b]pyridazine which had a melting point of 263° – 266°C.

EXAMPLE 47.

Preparation of
2-(5-Nitro-2-furyl)-4-(furfurylamino-methylene)-hydrazino-pyrimidine.

2.2 g. 2-(5-nitro-2-furyl)-4-hydrazino-pyrimidine were stirred for 3 hours at 100°C. with 1.7 g. of the imino ether (b.p. 80° – 82°C/11 mm.Hg.) obtainable from furfurylamine and ortho-formic acid ethyl ester, the reaction being carried out in 22 ml. dioxan. Thereafter, the reaction mixture was filtered with activated charcoal and the filtrate evaporated. The evaporation residue was stirred up with ether. There were thus obtained 2.8 g. of thin layer chromatographically uniform, red-brown 2-(5-nitro-2-furyl)-4-(furfurylamino-methylene)-hydrazino-pyrimidine which melted, with decomposition, at 174° – 176°C. The elementary analysis agreed with the given structure.

EXAMPLE 48

Preparation of
3-(5-Nitro-2-furyl)-6-(carbethoxymethylamino-methylene)-amino-s-triazolo[4,3-b] pyridazine 0.6 g. crude 3-(5-nitro-2-furyl)-6-ethoxymethyleneamino-s-triazolo[4,3-b]pyridazine, dissolved in 12 ml hot dioxan, were mixed, while stirring, at 50° – 60°C. with 0.3 ml. ethyl aminoacetate, the reaction mixture further stirred for 15 minutes at this temperature and the solid product which precipitates then filtered off with suction, washed with dioxan and ether and recrystallized (0.62 g) from 8 ml. of a mixture of 80% dioxan and 20% dimethyl formamide, with the use of active charcoal, 0.46 g. of the desired, light-sensitive 3-(5-nitro-2-furyl)-6-(carbethoxymethylamino-methylene)-amino-s-triazolo[4,3-b]pyridazine thereby being obtained; it has a melting point of 205° – 208°C. (decomp.)

The starting material was obtained in the following manner: 20 g. 3-(5-nitro-2-furyl)-6-amino-s-triazolo[4,3-b]pyridazine were heated with 400 ml. triethyl orthoformate and 60 ml acetate anhydride for 1.5 hours under reflux, then cooled and diluted with 600 ml. benzene. 400 – 600 ml. ether were then added thereto, then mixed with active charcoal and stirred for some time, filtered with suction, thoroughly washed with benzene and the filtrate carefully evaporated in a vacuum to a volume of about 250 ml. The precipitated crystals were filtered off with suction, washed with isopropanol and ether and dried in a vacuum at 80°C. There were thus obtained 12.3 g. 3-(5-nitro-2-furyl)-6-ethoxymethyleneamino-s-triazolo[4,3-b]pyridazine (m.p. 190° – 192°C.); the compound should be stored with the exclusion of air. After recrystallization from a mixture of 70% benzene and 30% dioxan, the compound has a melting point of 193°–195°C.

EXAMPLE 49

Preparation of 3-(5-Nitro-2-furyl)-5-(carbethoxymethylamino-methylene)-amino-1,2,4-thiadiazole 1.07 g. crude 3-(5-nitro-2-furyl)-5-ethoxymethyleneamino-1,2,4-thiadiazole (m.p. 129°–160°C) (obtained from 3-(5-nitro-2-furyl)-5-amino-1,2,4-thiadiazole and excess triethyl orthoformate by boiling under reflux for 2 hours) was dissolved in a mixture of benzene and dioxan (1:1), while heating, 0.6 ml. ethyl aminoacetate were added thereto, while stirring, at 10°C., the product formed was then filtered off with suction, after stirring for one hour at 10°C., washed with benzene and ether and the product thus obtained (0.91 g., m.p. 180°–186°C.) recrystallized from 5 ml. dioxan, 0.59 g. of the desired 3-(5-nitro-2-furyl)-5-(carbethoxymethylamino-methylene)-amino-1,2,4-thiadiazole thereby being otained; m.p. obtained; 194°–196°C.

The starting material was obtained in the following manner: 32.7 g. crude 5-nitro-2-furaminidine hydrochloride (m.p. 232°–234°C.) are suspended in 910 ml. anhydrous acetone, 32 g. trichloromethyl-sulphenyl chloride added thereto, while stirring, whereafter 91 ml. triethylamine were added dropwise at 0°–5°C., over the course of 20 minutes, the reaction mixture then being stirred for 40 minutes at this temperature and subsequently for 2 hours at 50°–55°C. After cooling, the precipitated triethylamine hydrochloride was filtered off with suction, the filtrate was evaporated in a vacuum, the evaporation residue was triturated with water, the pH was adjusted to about 5 with sodium acetate, insoluble material was filtered off with suction, the still moist material was triturated with methanol, filtered off with suction, thereafter washed with methanol and, after drying in a vacuum at 80°C., there were obtained 17.5 g. crude 3-(5-nitro-2-furyl)-5-chloro-1,2,4-thiadiazole (m.p. 160°–162°C.), which can be recrystallized from methanol: dioxan (1:1), with the use of active charcoal; m.p. 167°–168°C.

13.8 g. of the crude product thus obtained were dissolved in a mixture of 500 ml. ethanol and 150 ml. dioxan, gaseous ammonia was passed therethrough for 4 hours at 70°C., while stirring, the solution was mixed with active charcoal, suction filtered while still hot, the clear filtrate was evaporated in a vacuum to about 70 ml. and the precipitated crystals were filtered off with suction and washed with ethanol and water and finally with ether, whereby there were obtained 7.5 g. crude 3-(5-nitro-2-furyl)-5-amino-1,2,4-thiadiazole; m.p. 277°–278°C. (decomp.)

EXAMPLE 50

Preparation of 3-(5-Nitro-2-furyl)-6-(acetamidomethylene)-amino-s-triazolo[4,3-b]pyridazine 0.57 g. 3-(5-nitro-2-furyl)-6-(aminomethylene)-amino-s-triazolo[4,3-b]pyridazine was stirred for 2 hours at 60°C. with 12 ml. acetic anhydride, then filtered with suction and the product obtained washed with acetic anhydride and ether and recrystallized (0.55 g.; m.p. 250°–260°C., foams) from 7 ml. dioxan-dimethyl formamide (1:1), 0.35 g. of the desired 3-(5-nitro-2-furyl)-6-(acetamidomethylene)-amino-s-triazolo[4,3-b]pyridazine thereby being obtained (m.p. 258°–260°C. (decomp.)).

The starting material was obtained in the following manner: 0.9 g. 3-(5-nitro-2-furyl)-6-ethoxymethyleneamino-s-triazolo[4,3-b]pyridazine are dissolved in 20 ml. anhydrous dioxan, gaseous ammonia passed therethrough for 5 minutes at 50°C., the reaction mixture then stirred for 15 minutes at this temperature and cooled and solids were filtered off with suction and washed with dioxan to give 0.77 g. 3-(5-nitro-2-furyl)-6-(aminomethyleneamino)-s-triazolo[4,3-b]pyridazine which, after recrystallization from 35 ml. dimethyl formamide, was obtained in the form of an intensive yellow powder; m.p. 269°–272°C. (foams).

EXAMPLE 51

PREPARATION OF 3-(5-Nitro-2-furyl)-6-(methylcarbamoylamidomethylene)-amino-s-triazolo[4,3-b]pyridazine.

0.46 g. methyl isocyanate, dissolved in 20 ml. anhydrous pyridine, was mixed with 1.08 g. 3-(5-nitro-2-furyl)-6-(aminomethylene)-amino-s-triazolo[4,3-b]pyridazine, whereafter the reaction mixture was stirred at 100°C. for 1 hour, cooled and the solid materials then filtered off with suction and washed with pyridine and ether to give 1.1 g. of the desired 3-(5-nitro-2-furyl)-6-(methylcarbamoylaminomethylene)-amino-s-triazolo[4,3-b]pyridazine; m.p. 234°–236°C. (decomp).

EXAMPLE 52

Preparation of 3-(5-Nitro-2-thieny)-6-(cyclohexylaminomethylene)-amino-s-triazolo[4,3-b]pyridazine A solution of 1.2 g. 3-(5-nitro-2-thienyl)-6-ethoxymethyleneamino-s-triazolo[4,3-b]pyridazine in 30 ml. dioxan, with a temperature of 60°C., was mixed dropwise with 0.7 ml. cyclohexylamine. After stirring for 15 minutes, the reaction mixture was cooled, whereby crystallization commences. After filtering off with suction and washing with dioxan and ether, there were obtained, after drying, 0.9 g. of the desired 3-(5-nitro- 2-thienyl)-6-(cyclohexylaminomethylene)-amino-s-triazolo[4,3-b]pyridazine, which is thin layer chromatographically uniform and is in the form of yellow crystals; m.p. 212°–215°C. The elementary analyses and spectra confirm the given structure.

The starting material was obtained in the following manner: 5-nitrothiophene-2-aldehyde was reacted in alcohol with 3-hydrazino-6-chloropyridazine to give the corresponding hydrazone (m.p. 283°C., decomp.). This was oxidatively cyclised in glacial acetic acid with lead tetraacetate. The 3-(5-nitro-2-thienyl)-6-chloro-s-triazolo[4,3-b]pyridazine thus obtained (m.p. 215°–217°C) was aminated in the usual way be reaction with potassium phthalimide and subsequent acidic fission to give 3-(5-nitro-2-thienyl)-6-amino-s-triazolo[4,3-b]pyridazine. This amino compound heated with triethyl orthoformate in the presence of acetic anhydride, whereby 3-(5-nitro-2-thienyl)-6-ethoxymethyleneamino-s-triazolo[4,3-b]pyridazine was obtained; m.p. 180°–182°C.

EXAMPLE 53

Preparation of
3-(5-Nitro-2-furyl)-6-(cyclohexylaminoethylene)-amino-s-triazolo[4,3-b]pyridazine 0.9 g. 3-(5-nitro-2-furyl)-6-ethoxymethyleneamino-s-triazolo[4,3-b]pyridazine was dissolved in 15 ml. hot dioxan, mixed at 50°–60°C., with stirring, with 0.6 ml. cyclohexylamine, maintained at this temperature for 15 minutes, cooled to ambient temperature and mixed with 50 ml. ether and the precipitated material filtered off with suction (0.66 g.) and recrystallized from 20 ml. dioxan-benzene (1:1), with the use of active charcoal, whereby 0.45 g. of the desired 3-(5-nitro-2-furyl)-6-(cyclohexylaminomethylene)-amino-s-triazolo[4,3-b]pyridazine were obtained; m.p. 201°C.

EXAMPLE 54

Preparation of
3-(5-Nitro-2-furyl)-6-(4-hydroxypiperidinomethylene)-amino-s-triazolo[4,3-b]pyridazine 0.9 g. 3-(5-nitro-2-furyl)-6-ethoxymethyleneamino-s-triazolo[4,3-b]pyridazine were dissolved in 15 ml. hot dioxan mixed at 50°–60°C, with 0.6 g. 4-hydroxypiperidine, allowed to react at this temperature for 15 minutes, the solid material then filtered off with suction at ambient temperature and washed with dioxan and ether to give 0.83 g. of the desired 3-(5-nitro-2-furyl)-6-(4-hydroxypiperidinomethylene)-amino-s-triazolo[4,3-b]pyridazine; m.p. 230°–236°C.

EXAMPLE 55

Preparation of
3-(5-Nitro-2-furyl)-6-(4-β-hydroxyethyl-piperidinomethylene)-amino-s-triazolo[4,3-b]pyridazine From 0.9 g. 3-(5-nitro-2-furyl)-6-ethoxymethyleneamino-s-triazolo[4,3-b]pyridazine and 0.77 g. 4-(β-hydroxyethyl)-piperidine, there were obtained, in a manner analogous to that described in Example 54, 0.98 g. of the desired 3-(5-nitro-2-furyl)-6-(4-β-hydroxyethyl-piperidinomethylene)-amino-s-triazolo[4,3-b]pyridazine; m.p. 208°–213°C.

EXAMPLE 56

Preparation of
3-(5-Nitro-2-thienyl-6-(morpholinomethylene)-amino-s-triazolo[4,3-b]pyridazine 2.4 g. N-formyl-morpholine were dissolved in 9 ml. dioxan, 1.9 ml. phosphorus oxychloride were added thereto dropwise and the solution obtained was stirred for 1 hour at 25°C. Thereafter, 2.6 g. 3-(5-nitro-2-thienyl)-6-amino-s-triazolo[4,3-b]pyridazine were added and thereafter rinsed with 6 ml. dioxan. The suspension obtained, which is of low viscosity, was further stirred for 1.5 hours at 35°–40°C. and left to stand overnight at ambient temperature. The solid material was then filtered off with suction, washed with dioxan and the crystals obtained were introduced into ice water. After neutralization with dilute aqueous ammonia solution, the reaction mixture was again filtered with suction, and the solid material obtained was washed with water and methanol to give 1.7 g. (48% of theory) 3-(5-nitro-2-thienyl)-6-(morpholinomethylene)-amino-s-triazolo[4,3-b]pyridazine. After recrystallization from dimethyl formamide, with the addition of charcoal, the product was obtained in the form of yellow crystals which melt at 228°–231°C. The elementary analyses and spectra confirm the structure.

The starting material was prepared in the following manner: 5-nitro-thiophene-2-aldehyde was reacted with 3-hydrazino-6-chloropyridazine to give the corresponding hydrazone (m.p. 283°C., decomp.). This was then oxidatively cyclised in glacial acetic acid with lead tetraacetate. The 3-(5-nitro-2-thienyl)-6-chloro-s-triazolo[4,3-b]pyridazine (m.p. 215°–217°C) thus obtained was aminated in the usual manner by reaction with potassium phthalimide and subsequent acidic fission. The crude product thus obtained has a melting point of 240°C.

EXAMPLE 57

Preparation of
3-(5-Nitro-2-thienyl)-6-(dimethylaminomethylene)-amino-s-triazolo[4,3-b]pyridazine 0.8 g. 3-(5-nitro-2-thienyl)-6-amino-s-triazolo[4,3-b]pyridazine was suspended in a mixture of 3 ml. N,N-dimethylformamide and 1. ml. N,N-dimethyl formamide-diethyl acetal and heated, while stirring, on a waterbath for two hours. Thereafter, the reaction mixture was cooled, solid material was filtered off with suction and the residue is washed with N,N-dimethyl formamide. There was thus obtained 0.4 g. (41% of theory) 3-(5-nitro-2-thienyl)-6-(diethylaminomethylene)-amino-s-triazolo[4,3-b]pyridazine (m.p. 247°–249°C). After recrystallization from N,N-dimethyl-formamide, with the addition of charcoal the product was obtained in the form of yellow crystals which melt at 249°–252°C. The elementary analyses and spectra confirm the structure.

EXAMPLE 58

Preparation of
3-(5-Nitro-2-furyl)-6-[(2-acetaminoethyl)-aminomethylene]-amino-s-triazolo[4,3-b]-pyridazine In a manner analogous to that described in Example 48, from 3-(5-nitro-2-furyl)-6-ethoxymethyleneamino-s-triazolo[4,3-b]pyridazine and N-acetyl-ethylenediamine in dioxan, there was obtained the desired 3-(5- nitro-2-furyl)-6-[(2-acetaminoethyl)-aminomethylene]-amino-s-triazolo[4,3-b]pyridazine in the form of yellow crystals which melt at 176°–181°C. Elementary analyses and spectra confirm the given structure.

The bacteriostatic activity of the compounds in accordance with the invention was evaluated in vitro and in vivo. The following comparison compound and compounds according to the invention were used in the tests:

| Compound No. | Chemical Name |
| --- | --- |
| A (Comparison Compound) | N-(5-Nitrofuryliden)-1-aminohydantoine (sold under the trade name "Furadantin" by Norwich Pharmacal Co.) |
| 1 | 3-(5-Nitro-2-furyl)-6-(dimethylaminomethylenamino)-s-triazolo-[4,3-b]pyridazine |
| 2 | 5-(5-Nitro-2-furyl)-3-(dimethylaminomethylenamino)-1,2,4-triazole |
| 3 | N-[3-(5-Nitro-2-furyl)-6-(s-triazolo[4,3-b]pyridazinyl)]-N',N'-dimethylacetamidine |
| 4 | 1-Methyl-2-[3-(5-nitro-2-furyl)-6-(s-triazolo [4,3-b]pyridazinyl)]-imino-pyrrolidine |
| 5 | 3-(5-Nitro-2-furyl)-6-(dimethylaminomethylenhydrazino)-s-triazolo[4,3-b]pyridazine |
| 6 | 3-(5-Nitro-2-furyl)-6-[(1-piperidinyl-methyl)-methylenamino]-s-triazolo[4,3-b]pyridazine |
| 7 | 3-(5-Nitro-2-furyl)-6-(morpholino-methylene)-amino-s-triazolo [4,3-b]-pyridazine |
| 8 | N-[3-(5-Nitro-2-furyl)-6-(s-triazolo-[4,3-b]pyridazinyl)-N',N'-diethylacetamidine |
| 9 | 3-(5-Nitro-2-furyl)-6-[1-(1-pyrrolidinyl)-ethylidene]-amino-s-triazolo[4,3-b]pyridazine |
| 10 | 4-(5-Nitro-2-furyl)-2-(dimethylaminomethylene)-amino-thiazole |
| 11 | 3-(5-Nitro-2-furyl)-6-[1-(morpholino)-ethylidene]-amino-s-triazolo[4,3-b]pyridazine |
| 12 | 1-Methyl-2-[3-(5-nitro-2-furyl)-5-(1,2,4-thiadiazolyl)]-imino-pyrrolidine |
| 13 | 3-(5-Nitro-2-furyl)-5-(1-dimethylaminoethylidene)-amino-1,2,4-thiadiazole |
| 14 | 2-(5-Nitro-2-furyl)-4-methylmercapto-6-(dimethylamino-methylene)-amino-s-triazine |
| 15 | 3-(5-Nitro-2-furyl)-5-(morpholinomethyleneamino-1,2,4-thiadiazole |
| 16 | 3-(5-Nitro-2-furyl)-6-(1-dimethylamino-ethylidene)-hydrazino-s-triazolo[4,3-b]pyridazine |
| 17 | 3-(5-Nitro-2-furyl)-6-(piperidino-methylenamino)-2-triazolo[4,3-b]pyridazine |
| 18 | 3-(5-Nitro-2-furyl)-6-(methylamino-methylene)-amino-s-triazolo[4,3-b]pyridazine |
| 19 | 3-(5-Nitro-2-furyl)-6-(aminomethylene-amino)-s-triazolo[4,3-b]pyridazine |
| 20 | 3-(5-Nitro-2-furyl)-6-[(N,N-di-d hydroxyethyl-amino)-methylene]-amino-s-triazolo[4,3-b]pyridazine |
| 21 | 3-(5-Nitro-2-furyl)-6-(4-methyl-1-piperazinyl-methylenamino)-s-triazolo-[4,3-b]pyridazine |
| 22 | 3-(5-Nitro-2-furyl)-6-[(2-N,N-dimethyl-hydrazino)-methylene]-amino-s-triazolo[4,3-b]pyridazine |
| 23 | 3-(5-Nitro-2-furyl)-6-[(N-β-hydroxyethyl-N-methyl-amino)-methylene]-amino-s-triazolo[4,3-b]pyridazine |
| 24 | 1-Methyl-2-[3-(5-nitro-2-furyl)-6-(s-triazolo[4,3-b]pyridazinyl)]-hydrazono-pyrrolidine |
| 25 | 3-(5-Nitro-2-furyl)-5-(methylaminomethylene)-amino-1,2,4-thiadiazole |
| 26 | 3-(5-Nitro-2-furyl)-6-(dimethylaminomethylene-amino)-s-triazolo-[4,3-a]pyridine |
| 27 | 5-(5-Nitro-2-furyl)-3-(dimethylaminomethylene)-amino-s-triazolo-[4,3-d]thiadiazole-(1,2,4) |

-continued

| Compound No. | Chemical Name |
| --- | --- |
| 28 | 5-(5-Nitro-2-furyl)-3-(dimethylaminomethylene)-amino-s-triazolo[3,4-b]thiazole |
| 29 | 3-(5-Nitro-2-furyl)-5-(amino-methylene)-amino-1,2,4-thiadiazole |
| 30 | 5-(5-Nitro-2-furyl)-3-(piperidino-methylene)-amino-s-triazolo[3,4-b]thiazole m.p. 222–224°C |
| 31 | 1-Methyl-2-[3-(5-nitro-2-furyl)-6-(s-triazolo[4,3-b]pyridazinyl)]-hydrazono-piperidine |
| 32 | 3-(5-Nitro-2-furyl)-6-methyl-7-(or-5) dimethylamino-methylene)-amino-s-triazolo[4,3-a]pyrimidine |
| 33 | 3-(5-Nitro-2-furyl)-6-(N-methyl-N-phenylamino-methylene)-amino-s-triazolo[4,3-b]pyridazine |
| 34 | 3-(5-Nitro-2-furyl)-6-(IV-p-methoxyphenyl-amino-methylene)-amino-s-triazolo [4,3-b]pyridazine |
| 35 | 3-(5-Nitro-2-furyl)-6-(N-p-oxyphenyl-amino-methylene)-amino-s-triazolo [4,3-b]pyridazine |
| 36 | N'-[2-(5-Nitro-2-furyl)-4-methyl-6-pyrimidinyl]-N,N-dimethyl-formamidine |
| 37 | 3-(5-Nitro-2-furyl)-6-(dimethylamino-methylene)-amino-pyridazine |
| 38 | 2-(5-Nitro-2-furyl)-4-(2-dimethylamino-methylene)-hydrazino-pyrimidine |
| 39 | 1-Methyl-2-[2-(5-nitro-2-furyl)-4-pyrimidinyl]-hydrazono-pyrrolidine |
| 40 | 2-(5-Nitro-2-furyl)-4-[2-(dimethylamino-methoxymethyl)methylene]-hydrazino-pyrimidine |
| 41 | 2-(5-Nitro-2-furyl)-4-azido-6-(2-dimethyl-amino-methylene)-hydrazinopyrimidine |
| 42 | 2-(5-Nitro-2-furyl)-4-chlor-5-methyl-6-(2-dimethylaminomethylene)-hydrazino-pyrimidine |
| 43 | 2-(5-Nitro-2-furyl)-4-[2-(morpholino-methyl)-methylene]-hydrazino-pyrimidine |
| 44 | 2-(5-Nitro-2-furyl)-4-(morpholino-methylene)-hydrazino-pyrimidine |
| 45 | 2-(5-Nitro-2-furyl)-4-(dimethylamino-methylene)-amino-pyrimidine |
| 46 | 2-(Dimethylamino-methylene)-amino-4-(5-nitro-2-furyl)-6-ethoxy-pyrimidine |
| 47 | 2-(5-Nitro-2-furyl)-4-methyl-6-(dimethylamino-methylene)-hydrazino-pyrimidine |
| 48 | 1-Methyl-2-[2-(5-nitro-2-furyl)-4-methyl-6-pyrimidinyl]-hydrazono-piperidine |
| 49 | 3-(Dimethylamino-methylene)-amino-6-(5-nitro-2-furyl)-s-triazolo-[4,3-b]pyridazine |
| 50 | 2-(5-nitro-2-furyl)-4-methyl-6-(diethylamino-methylene)-hydrazino-pyrimidine |
| 51 | 2-(5-Nitro-2-furyl)-4-(diethylamino-methylene)-amino-pyrimidine |
| 52 | 2-(5-Nitro-2-furyl)-4-methyl-6-[1-(morpholino)-ethylidene]-hydrazino-pyrimidine |
| 53 | 5-Cyano-6-dimethylaminomethylenamino-2-methyl-4-(5-nitro-2-furyl)-pyrimidine |
| 54 | 5-(Dimethylamino-methylene)-amino-2-(5-nitrofuryl-2)-pyrimidine |
| 55 | 5-(Morpholinomethylene)-amino-2-(5-nitrofuryl-2)-pyrimidine |
| 56 | 2-(Dimethylaminomethylene)-amino-6-chlor-4-(5-nitrofuryl-2)-pyrimidine |
| 57 | 6-(Dimethylaminomethylene)-amino-2-methyl-4-(5-nitrofuryl-2)-pyrimidine |
| 58 | 6-Dimethylaminomethylene)-hydrazino-2-methyl-4-(5-nitrofuryl-2)-pyrimidine |
| 59 | 6-[1-(Dimethylaminoethylidene)]-hydrazino-2-methyl-4-(5-nitrofuryl-2)-pyrimidine |
| 60 | 2-Methyl-6-(1-morpholino-ethylidene)-hydrazino-4-(5-nitrofuryl-2)-pyrimidine |
| 61 | 2-Methyl-6-(morpholinomethylene)-hydrazino-4-(5-nitrofuryl-2)-pyrimidine |
| 62 | 6-(Diethylaminomethylene)-hydrazino-2-methyl-4-(5-nitrofuryl-2)-pyrimidine |
| 63 | 5-(Diethylaminomethylene)-amino-2-(5-nitrofuryl-2)-pyrimidine |
| 64 | 6-(Diethylaminoethylene)-amino-2-methyl-4-(5-nitrofuryl-2)-pyrimidine |
| 65 | 2,8-Dimethyl-5-(morpholinomethylene)-amino-7-(5-nitrofuryl-2)-s-triazolo |

-continued

| Compound No. | Chemical Name |
|---|---|
| 66 | 2,8-Dimethyl-5-(diethylaminomethylene)-amino-7-(5-nitrofuryl-2)-s-triazolo[2,3-c]pyrimidine |
| 67 | 3-(5-Nitro-2-furyl)-6-(carbaethoxy-methylamino-methylene)-amino-s-triazolo[4,3-b]pyridazine |
| 68 | 3-(5-Nitro-2-furyl)-6-(acetamido-methylene)-amino-s-triazolo[4,3-b]pyridazine |
| 69 | 3-(5-Nitro-2-furyl)-6-(4-hydroxy-piperidino-methylene)-amino-s-triazolo[4,3-b]pyridazine |
| 70 | 3-(5-Nitro-2-furyl)-6-(4-β-hydroxy-ethyl-piperidino-methylene)-amino-s-triazolo[4,3-b]pyridazine |
| 71 | 3-(5-Nitro-2-furyl)-6-(cyclohexyl-aminomethylene)-amino-s-triazolo-[4,3-b]pyridazine |
| 72 | 3-(5-Nitro-2-furyl)-6-(methyl-carbamoyl-amidomethylene)-amino-s-triazolo[4,3-b]pyridazine |
| 73 | 3-(5-Nitro-2-furyl)-6-[(2-acetamino-ethyl)-aminomethylene]-amino-s-triazolo[4,3-b]pyridazine |

The absolute bacteriostatic minimal concentration in vitro of the test compounds, for the different bacterial species indicated, is set out in micrograms of test compound per mililiter in the following Table I.

In addition, the compounds were evaluated with respect to their bacteriostatic activity against Escherichia coli in the excreted urine of rats following oral administration.

In these tests, 20 milligrams of test compound were used per kg of rat body weight. Each experimental value reported is the average of tests on six (or nine) rats and represents the maximal dilution (with water) to which the excreted urine from treated (i.e., after oral administration of test compound) animals could be subjected while still having bacteriostatic properties. The excreted urine tests were carried out 22 hours after administration of test compound on the basis of 50 (or 75) mililiter samples of urine.

The results of the latter experiments are set out in Table II.

TABLE I

ABSOLUTE BACTERIOSTATIC ACTIVITY IN VITRO (MINIMAL CONCENTRATION IN $\mu g/ml$)

| Compound No. | Staphylococcus aureus, SG 511 | Streptococcus pyogenes Aronson | Streptococcus faecalis | Escherichia coli | Proteus mirabilis | Pseudomonas aeruginosa |
|---|---|---|---|---|---|---|
| A | 16 | 4 | 16 | 8*<br>4 | 128**<br>128 | |
| 1 | 1 | 0.25 | 0.25 | 0.062 | 4 | 1 |
| 2 | 4 | 2 | 8 | 2 | >256 | >256 |
| 3 | 4 | 4 | 0.25 | 0.25 | >16 | >16 |
| 4 | 2 | 0.5 | 0.062 | 0.125 | >16 | >8 |
| 5 | 8 | 0.5 | 2 | 0.125 | 128 | 32 |
| 6 | 2 | 4 | 0.25 | 0.5 | 128 | >64 |
| 7 | | | 1 | 0.031 | 4 | 2 |
| 8 | | | 0.25 | 0.5 | >256 | >128 |
| 9 | | | 0.25 | 0.5 | >256 | >128 |
| 10 | | | 2 | 0.25 | >256 | >128 |
| 11 | | | 0.125 | 0.125 | >256 | 8 |
| 12 | | | 2 | 0.5 | >256 | >256 |
| 13 | | | 8 | 0.25 | >256 | >256 |
| 14 | | | 0.5 | 0.5 | >256 | >256 |
| 15 | | | 8 | 0.125 | >256 | 128 |
| 16 | | | 2 | 0.125 | >256 | 32 |
| 17 | | | 0.062 | 0.062 | 8 | 0.5 |
| 18 | | | 2 | 0.062 | 4 | 1 |
| 19 | | | 1 | 0.016 | 2 | 0.5 |
| 20 | | | 4 | 0.062 | 4 | 2 |
| 21 | | | 0.25 | 0.062*<br>0.031 | 4**<br>2 | 0.5 |
| 22 | | | 2 | 0.031 | >16 | 2 |
| 23 | | | 0.5 | 0.016 | 2 | 1 |
| 24 | | | 2 | 0.062 | >256 | 32 |
| 25 | | | 1 | 0.031 | >256 | 16 |
| 26 | | | 0.125 | 0.062 | 32 | 4 |
| 27 | | | 2 | 8 | >16 | >16 |
| 28 | | | 0.008 | 0.031 | 8 | 4 |
| 29 | | | 1 | 0.062 | 256 | 128 |
| 30 | | | 0.016 | 1 | 256 | 128 |
| 31 | | | 0.5 | 0.016 | 256 | 2 |
| 32 | | | 1 | 0.5 | 64 | 32 |
| 33 | | | 1 | 0.062 | >16 | 4 |
| 34 | | | 4 | 0.062 | 8 | 2 |
| 35 | | | 1 | 0.031 | 2 | 1 |
| 36 | 2 | 0.5 | 0.25 | 0.125 | 32 | 16 |
| 37 | 8 | 64 | 0.5 | 0.125 | 16 | 32 |
| 38 | 0.5 | 8 | 4 | 1 | 256 | 128 |
| 39 | 8 | 16 | 16 | 2 | >128 | 128 |
| 40 | 4 | 16 | 4 | 4 | 256 | 128 |
| 41 | 0.5 | 1 | 0.25 | 2 | >256 | 128 |
| 42 | 4 | 128 | 8 | 1 | >128 | >64 |
| 43 | 4 | 128 | 16 | 2 | 256 | 64 |
| 44 | 4 | 4 | 2 | 1 | >128 | 64 |
| 45 | | | 4 | 0.125 | 16 | 8 |
| 46 | | | 0.5 | 0.5 | >256 | 64 |
| 47 | | | 4 | 1 | >256 | >64 |
| 48 | | | 4 | 1 | >256 | >64 |
| 49 | | | 2 | 2 | 256 | 16 |
| 50 | | | 4 | 1 | >256 | >256 |
| 51 | | | 2 | 0.125 | 64 | 8 |
| 52 | | | 4 | 4 | >256 | >128 |

TABLE I-continued

| Compound No. | ABSOLUTE BACTERIOSTATIC ACTIVITY IN VITRO (MINIMAL CONCENTRATION IN µg/ml) | | | | | |
|---|---|---|---|---|---|---|
| | Staphylococcus aureus, SG 511 | Streptococcus pyogenes Aronson | Streptococcus faecalis | Escherichia coli | Proteus mirabilis | Pseudomonas aeruginosa |
| 53 | 0.125 | 0.25 | 0.125 | 1 | 32 | 8 |
| 54 | | | 2 | 0.25 | 64 | 4 |
| 55 | | | 2 | 0.25 | 128 | 8 |
| 56 | | | 0.25 | 0.5 | 64 | 8 |
| 57 | | | 0.5 | 0.125 | 16 | 8 |
| 58 | | | 1 | 0.125 | 16 | 4 |
| 59 | | | 2 | 0.5 | 256 | >64 |
| 60 | | | 2 | 1 | 256 | >64 |
| 61 | | | 0.5 | 0.5 | 64 | 32 |
| 62 | | | 4 | 2 | >256 | 256 |
| 63 | | | 2 | 0.25 | >256 | 32 |
| 64 | | | 0.25 | 0.25 | >256 | 16 |
| 65 | | | 0.004 | 0.5 | 256 | >128 |
| 66 | | | 0.062 | 2 | >128 | >64 |
| 67 | | | 4 | 0. 25* | 8** | 4 |
| | | | | 0.125 | 8 | |
| 68 | | | 0.5 | 0.062* | 1** | 0.5 |
| | | | | 0.031 | 1 | |
| 69 | | | 1 | 0.25* | 8 | 0.5 |
| | | | | 0.062 | 4** | |
| 70 | | | 0.5 | 0.25* | 4 | 0.5 |
| | | | | 0.062 | 2** | |
| 71 | | | 1 | 0.125* | 4** | 1 |
| | | | | 0.062 | 4 | |
| 72 | | | 0.5 | 0.008* | 1** | 0.5 |
| | | | | 0.004 | 1 | |
| 73 | | | 2 | 0.062* | 8** | 1 |
| | | | | 0.031 | 8 | |

\* Value with asterisk - Escherichia coli (18)
Value without asterisk - Escherichia coli (106)
\*\*Value with asterisks - Proteus mirabilis (279)
Value without asterisks - Proteus mirabilis (298)

TABLE II

| Compound No. | Maximum Bacteriostatic Dilution (Volume Ratio) |
|---|---|
| A | 1:54 |
| | 1:30 |
| | 1:41 |
| | 1:19 |
| | 1:40 |
| | 1:21 |
| | 1:1100 |
| 1 | |
| | 1:960 |
| | 1:373 |
| 3 | |
| | 1:252 |
| | 1:920 |
| 4 | |
| | 1:1380 |
| 5 | 1:178 |
| | 1:433 |
| 6 | |
| | 1:584 |
| | 1:1300 |
| 7 | |
| | 1:667 |
| 8 | 1:600 |
| 9 | 1:2133 |
| 11 | 1:257 |
| | 1:196 |
| 13 | 1:123 |
| | 1:75 |
| 16 | 1:260 |
| | 1:256 |
| 17 | 1:667 |
| 19 | 1:333 |
| 21 | 1:667 |
| | 1:853 |
| 22 | 1:300 |
| 24 | 1:179 |
| 25 | 1:95 |
| 31 | 1:101 |
| 32 | 1:85 |
| 33 | 1:107 |
| 35 | 1:79 |
| 36 | 1:264 |
| | 1:230 |
| 38 | 1:21 |
| | 1:43 |
| 40 | 1:32 |
| | 1:23 |

TABLE II-continued

| Compound No. | Maximum Bacteriostatic Dilution (Volume Ratio) |
|---|---|
| 44 | 1:68 |
| | 1:88 |
| 45 | 1:251 |
| | 1:160 |
| 47 | 1:34 |
| 50 | 1:67 |
| 51 | 1:224 |
| 52 | 1:64 |
| 55 | 1:87 |
| 57 | 1:44 |
| 58 | 1:42 |
| 59 | 1:136 |
| 60 | 1:66 |
| 61 | 1:280 |
| 62 | 1:93 |
| 67 | 1:933 |
| | 1:576 |
| 68 | 1:736 |
| | 1:396 |
| 69 | 1:1460 |
| | 1:1500 |
| 70 | 1:368 |
| | 1:427 |
| 71 | 1:1420 |
| | 1:1360 |
| 72 | 1:450 |
| | 1:480 |
| | 1:45 |
| | 1:267 |
| 73 | 1:462 |
| | 1:592 |

The compounds of this invention are anti-microbials and have been found to be bactericidal to the pathogens found in surface infections, gram negative as well as gram positive. They additionally have utility as agents for routine treatment of acute and chronic bacterial infections of the urinary tract, including those caused by Proteus ap. Further they lend themselves because of their properties to use in the prevention or treatment of mixed surface infections or wounds, severe burns, cutaneous ulcers, pyodermas, osteomyelitis, preparation of wounds and burns for skin grafting and prevention of infection of grafts and donor sites.

The new compounds according to the present invention can be administered in liquid or solid form either orally or parenterally by admixture with a solid or liquid pharmaceutical diluent or carrier. As injection medium, there is preferably used water which contains the stabilizing agents, solubilizing agents and/or buffers conventional in injection solutions. Additives of this type include, for example, borate or tartrate buffers, ethanol, dimethyl sulfoxide, complex-forming agents (for example ethylene-diamine-tetraacetic acid), high molecular weight polymers (for example liquid polyethylene oxide) for viscosity regulation. Solid carrier materials include, for example, starch, lactose, mannitol, methyl-cellulose, talc, high-dispersed silicic acid, high molecular weight fatty acids (for example stearic acid), gelatine, agar-agar, calcium phosphate, magnesium stearate, animal and vegetable fats and solid, high molecular weight polymers (for example polyethylene glycols). Compositions suitable for oral administration can, if desired, contain flavoring and/or sweetening agents. For external administration, the new compounds according to the present invention can also be used in the form of powder or salves; for this purpose, they are mixed with, for example, powdered, physiologically compatible diluents or with conventional salve bases.

The compounds of the invention can be employed in the form of aqueous solutions or suspensions thereof, as for instance, in the form of an 0.01 to 0.05% aqueous suspension or solution; in the form of solutions in non-aqueous, hygroscopic liquid vehicles such as polyethylene glycol, for instance 0.1–0.5% solutions in polyethylene glycol; incorporation into a water-soluble ointment-like base (concentration 0.1–0.5%) or in a powder base composed for instance of water-soluble polyethylene glycols (concentration 0.1–0.5%); or in a form suitable for ingestion. Thus, a preferred form is a tablet containing 50–200 mg. of active compound. Depending on the conditions, symptomatic and laboratory responses 100–400 mg. per day can be administered. Another preferred form for orally administering the compounds of the invention is in the form of a suspension thereof in a water miscible flavored gel. Such gel can contain from 1 to 10 mg. of compound per cc.

It will be understood that the specification and examples are illustrative but not limitative of the present invention and that other embodiments within the spirit and scope of the invention will suggest themselves to those skilled in the art.

What is claimed is:
1. A compound of the formula

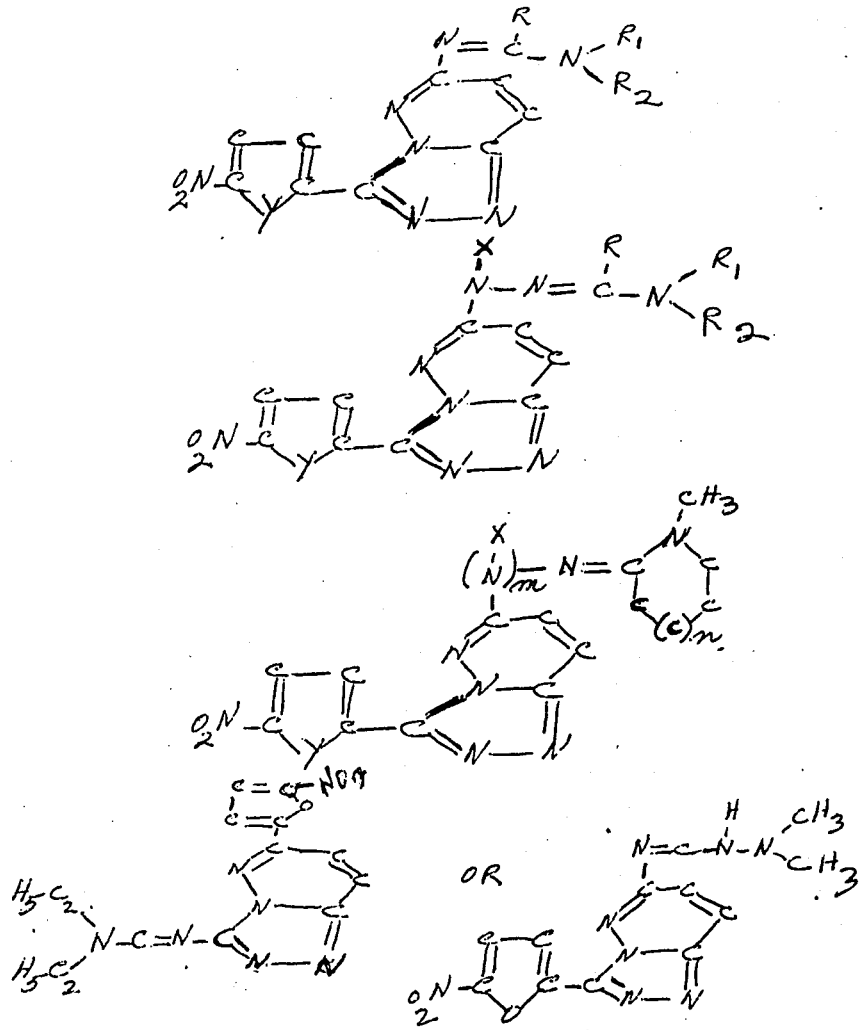

wherein R is H or —CH₃; X is H or

R₁ and R₂ are H, lower alkyl, OH, betahydroxyethyl, phenyl, hydroxyphenyl, methoxyphenyl, carbethoxy methyl, acetyl, methylcarbamoyl, cyclohexyl, acetylaminoethyl, 2-methyl-5-pyrimidyl or R₁ and R₂ together with the nitrogen atom to which they are attach form piperidino, morpholino, pyrrolidino, 4-methyl-piperazino, 4-hydroxy piperidino or 4-betahydroxy ethyl piperidino and Y is oxygen or sulfur, m and n are 0 or 1 or the pharmacologically acceptable acid addition salts thereof.

2. Compound as claimed in claim 1 designated 3-(5-nitro-2-furyl)-6-(dimethylamino-methylene-amino)-s-triazolo[4,3-b]pyridazine.

3. Compound as claimed in claim 1 designated 3-(5-nitro-2-furyl)-6-(morpholino-methylene)-amino-s-triazolo[4,3-b]pyridazine.

4. Compound as claimed in claim 1 designated 1-methyl-2-[3-(5-nitro-2-furyl)-6-(s-triazolo-[4,3-b]pyridazinyl)]-imino-pyrrolidine.

5. Compound as claimed in claim 1 designated 3-(5-nitro-2-furyl)-6-[1-pyrrolidinyl)-ethylidene]-amino-s-triazolo[4,3-b]pyridazine.

6. Compound as claimed in claim 1 designated N-[3-(5-nitro-2-furyl)-6-(s-triazolo[4,3-b]pyridazinyl)-]N'N'-diethyl-acetamidine.

7. Compound as claimed in claim 1 designated 3-(5-nitro-2-furyl)-6-(piperidino-methyleneamino)-s-triazolo[4,3-b]pyridazine.

8. Compound as claimed in claim 1 designated 3-(5-nitro-2-furyl)-6-[(1-piperidinyl-methyl)-methyleneamino]-s-triazolo[4,3-b]pyridazine.

9. Compound as claimed in claim 1 designated 3-(5-nitro-2-furyl)-6-(4-methyl-1-piperazinyl-methyleneamino)-s-triazolo[4,3-b]pyridazine.

10. Compound as claimed in claim 1 designated 3-(5-nitro-2-furyl)-6-(carbethoxymethylaminomethylene)-amino-s-triazolo[4,3-b]pyridazine.

11. Compound as claimed in claim 1 designated 3-(5-nitro-2-furyl)-6-(4-hydroxypiperidinomethylene)-amino-s-triazolo[4,3-b]pyridazine.

12. Compound as claimed in claim 1 designated 3-(5-nitro-2-furyl)-6-(cyclohexylaminomethylene)-amino-s-triazolo[4,3-b]pyridazine.

13. A therapeutic composition consisting essentially of an effective amount of a compound of claim 1 and a pharmaceutically acceptable carrier.

14. A method of combating infections of the urinary tract in mammals comprising Administering a compound of claim 1.

15. A composition of claim 13 in a dosage unit of 5 to 500 mg of a compound of claim 1.

* * * * *